US010874496B2

(12) United States Patent
Hunter

(10) Patent No.: US 10,874,496 B2
(45) Date of Patent: Dec. 29, 2020

(54) DEVICES, SYSTEMS AND METHODS FOR USING AND MONITORING IMPLANTS

(71) Applicant: CANARY MEDICAL INC., Vancouver (CA)

(72) Inventor: William L. Hunter, Vancouver (CA)

(73) Assignee: Canary Medical Inc., Vancouver (CA)

( * ) Notice: Subject to any disclaimer, the term of this patent is extended or adjusted under 35 U.S.C. 154(b) by 0 days.

(21) Appl. No.: 15/320,279

(22) PCT Filed: Jun. 25, 2015

(86) PCT No.: PCT/US2015/037803
§ 371 (c)(1),
(2) Date: Dec. 19, 2016

(87) PCT Pub. No.: WO2015/200704
PCT Pub. Date: Dec. 30, 2015

(65) Prior Publication Data
US 2017/0181825 A1 Jun. 29, 2017

Related U.S. Application Data

(60) Provisional application No. 62/017,099, filed on Jun. 25, 2014.

(51) Int. Cl.
A61F 2/00 (2006.01)
A61F 2/12 (2006.01)
(Continued)

(52) U.S. Cl.
CPC .......... A61F 2/0059 (2013.01); A61B 5/0031 (2013.01); A61B 5/01 (2013.01);
(Continued)

(58) Field of Classification Search
None
See application file for complete search history.

(56) References Cited

U.S. PATENT DOCUMENTS 5,413,604 A 5/1995 Hodge
5,626,581 A 5/1997 Staehlin et al.
(Continued)

FOREIGN PATENT DOCUMENTS

DE 19924676 11/2000
EP 2018825 1/2009
(Continued)

OTHER PUBLICATIONS

R.E. Ellis and T.M. Peters (Eds.); MICCAI 2003, LNCS 2879, pp. 754-761, 2003.*
(Continued)

Primary Examiner — Christopher Koharski
Assistant Examiner — James Moss
(74) Attorney, Agent, or Firm — BioMed IP

(57) ABSTRACT

Implants are provided, comprising the implant and a plurality of sensors. Briefly stated, implants (also sometimes referred to as 'devices' or medical devices') are provided comprising an implant along with one or more sensors to monitor the integrity, position and efficaciousness of the implant. The sensors may be positioned on the inside of the implant, within the body of the implant, or on the outer surface (or surfaces) of the implant, and/or between the implant and any device that might be utilized to deliver the implant (e.g., another implant, catheter, tunneling catheter, endoscope, balloon implant, or other medical device).

16 Claims, 5 Drawing Sheets

(51) Int. Cl.
  *A61B 5/00* (2006.01)
  *A61B 5/01* (2006.01)
  *A61B 5/06* (2006.01)
  *A61F 2/08* (2006.01)
  *A61F 2/18* (2006.01)
  *A61F 2/28* (2006.01)

(52) U.S. Cl.
  CPC ............ *A61B 5/067* (2013.01); *A61B 5/4312* (2013.01); *A61B 5/4851* (2013.01); *A61B 5/4866* (2013.01); *A61B 5/686* (2013.01); *A61B 5/6885* (2013.01); *A61F 2/08* (2013.01); *A61F 2/12* (2013.01); *A61F 2/186* (2013.01); *A61F 2002/0894* (2013.01); *A61F 2002/2807* (2013.01); *A61F 2250/0002* (2013.01); *A61F 2250/0096* (2013.01)

(56) References Cited

U.S. PATENT DOCUMENTS

| | | | |
|---|---|---|---|
| 5,833,603 A * | 11/1998 | Kovacs | A61B 1/00016 600/317 |
| 5,906,643 A | 5/1999 | Walker | |
| 6,019,794 A | 2/2000 | Walker | |
| 6,245,109 B1 | 6/2001 | Mendes et al. | |
| 6,358,202 B1 | 3/2002 | Arent | |
| 6,447,448 B1 | 9/2002 | Ishikawa | |
| 6,706,071 B1 | 3/2004 | Wolter | |
| 7,009,511 B2 | 5/2006 | Mazar et al. | |
| 7,097,662 B2 | 8/2006 | Evans, III et al. | |
| 7,130,695 B2 | 10/2006 | Czygan | |
| 7,141,026 B2 | 11/2006 | Aminian et al. | |
| 7,190,273 B2 | 3/2007 | Liao | |
| 7,383,071 B1 | 6/2008 | Russell et al. | |
| 7,450,332 B2 | 11/2008 | Pasolini et al. | |
| 7,463,997 B2 | 12/2008 | Pasolini et al. | |
| 7,553,923 B2 | 6/2009 | Williams et al. | |
| 7,559,951 B2 | 7/2009 | Disilvestro et al. | |
| 7,922,771 B2 | 4/2011 | Otto et al. | |
| 7,924,267 B2 | 4/2011 | Sirtori | |
| 8,029,566 B2 | 10/2011 | Lozier et al. | |
| 8,109,890 B2 | 2/2012 | Kamiar et al. | |
| 8,634,928 B1 | 1/2014 | O'Driscoll et al. | |
| 8,721,643 B2 | 5/2014 | Morgan et al. | |
| 8,876,739 B2 | 11/2014 | Salarian et al. | |
| 8,996,892 B1 | 3/2015 | Chu et al. | |
| 9,019,098 B2 | 4/2015 | Okano | |
| 9,307,932 B2 | 4/2016 | Mariani et al. | |
| 2002/0024450 A1 | 2/2002 | Townsend et al. | |
| 2003/0069644 A1 | 4/2003 | Kovacevic | |
| 2003/0074084 A1 | 4/2003 | Nakao | |
| 2003/0204267 A1 | 10/2003 | Hazebrouck | |
| 2004/0019382 A1 | 1/2004 | Amirouche et al. | |
| 2004/0019384 A1 | 1/2004 | Kirking | |
| 2004/0211580 A1 | 10/2004 | Wang | |
| 2004/0243148 A1 | 12/2004 | Wasielewski | |
| 2005/0010299 A1 | 1/2005 | Disilvestro | |
| 2005/0012610 A1 | 1/2005 | Liao et al. | |
| 2006/0009856 A1 | 1/2006 | Sherman | |
| 2006/0030945 A1 | 2/2006 | Wright | |
| 2006/0069403 A1 | 3/2006 | Shalon et al. | |
| 2006/0142670 A1 | 6/2006 | Disilvestro | |
| 2006/0184067 A1 | 8/2006 | Clark et al. | |
| 2006/0224088 A1 | 10/2006 | Roche | |
| 2006/0229730 A1 | 10/2006 | Railey | |
| 2006/0271199 A1 * | 11/2006 | Johnson | A61B 5/06 623/18.12 |
| 2006/0282168 A1 | 12/2006 | Sherman et al. | |
| 2007/0088442 A1 | 4/2007 | Cima et al. | |
| 2007/0089518 A1 | 4/2007 | Ericson | |
| 2007/0179739 A1 | 8/2007 | Donofrio et al. | |
| 2007/0233065 A1 | 10/2007 | Donofrio et al. | |
| 2007/0233267 A1 | 10/2007 | Amirouche et al. | |
| 2007/0238984 A1 | 10/2007 | Maschke et al. | |
| 2007/0238992 A1 | 10/2007 | Donofrio et al. | |
| 2008/0027679 A1 | 1/2008 | Shklarski | |
| 2008/0033527 A1 | 2/2008 | Nunez et al. | |
| 2008/0076972 A1 | 3/2008 | Dorogusker et al. | |
| 2008/0088436 A1 | 4/2008 | Reeves | |
| 2008/0208010 A1 | 8/2008 | Boyden et al. | |
| 2008/0214903 A1 | 9/2008 | Orbach | |
| 2008/0306325 A1 | 12/2008 | Burnett et al. | |
| 2009/0005708 A1 | 1/2009 | Johanson et al. | |
| 2009/0005876 A1 | 1/2009 | Dietz | |
| 2009/0012372 A1 * | 1/2009 | Burnett | A61B 5/076 600/300 |
| 2009/0048524 A1 | 2/2009 | Wildau | |
| 2009/0088756 A1 | 4/2009 | Anderson | |
| 2009/0119222 A1 | 5/2009 | O'Neil | |
| 2009/0157146 A1 | 6/2009 | Linder | |
| 2009/0264894 A1 | 10/2009 | Wasielewski | |
| 2009/0299228 A1 | 12/2009 | Lozier et al. | |
| 2010/0100011 A1 | 4/2010 | Roche | |
| 2010/0145337 A1 | 6/2010 | Janna et al. | |
| 2010/0191100 A1 | 7/2010 | Anderson et al. | |
| 2010/0204551 A1 | 8/2010 | Roche | |
| 2010/0204802 A1 | 8/2010 | Wilson et al. | |
| 2010/0285082 A1 | 11/2010 | Fernandez | |
| 2010/0287422 A1 | 11/2010 | Miyazaki | |
| 2011/0019595 A1 | 1/2011 | Magar et al. | |
| 2011/0054272 A1 | 3/2011 | Derchak | |
| 2011/0077736 A1 * | 3/2011 | Rofougaran | G06F 19/3418 623/8 |
| 2011/0098576 A1 * | 4/2011 | Hollstien | A61B 5/0082 600/476 |
| 2011/0098579 A1 | 4/2011 | Hollstien | |
| 2011/0196501 A1 | 8/2011 | Michelson | |
| 2011/0213221 A1 | 9/2011 | Roche | |
| 2011/0288805 A1 | 11/2011 | Aminian et al. | |
| 2011/0319755 A1 | 12/2011 | Stein et al. | |
| 2012/0035437 A1 * | 2/2012 | Ferren | A61B 1/041 600/302 |
| 2012/0123498 A1 | 5/2012 | Gross | |
| 2012/0123716 A1 | 5/2012 | Clark | |
| 2012/0130687 A1 | 5/2012 | Otto et al. | |
| 2012/0216611 A1 | 8/2012 | Stein | |
| 2012/0220839 A1 | 8/2012 | Stein et al. | |
| 2013/0079668 A1 | 3/2013 | Stein et al. | |
| 2013/0079671 A1 | 3/2013 | Stein et al. | |
| 2013/0079674 A1 | 3/2013 | Stein et al. | |
| 2013/0215979 A1 | 8/2013 | Yakovlev et al. | |
| 2013/0338770 A1 | 12/2013 | Boyden et al. | |
| 2014/0025338 A1 | 1/2014 | Blount et al. | |
| 2014/0135589 A1 | 5/2014 | Osorio | |
| 2014/0180697 A1 | 6/2014 | Torok et al. | |
| 2014/0257047 A1 | 9/2014 | Sillay | |
| 2014/0275849 A1 | 9/2014 | Acquista | |
| 2014/0296663 A1 * | 10/2014 | Boyden | A61B 5/4312 600/309 |
| 2014/0296978 A1 * | 10/2014 | Boyden | G01N 33/528 623/8 |
| 2015/0057775 A1 | 2/2015 | Dong | |
| 2015/0335290 A1 | 11/2015 | Hunter | |
| 2016/0029952 A1 | 2/2016 | Hunter | |
| 2016/0038087 A1 | 2/2016 | Hunter | |
| 2016/0192878 A1 | 7/2016 | Hunter | |
| 2017/0181825 A1 | 6/2017 | Hunter | |
| 2017/0189553 A1 | 7/2017 | Hunter | |
| 2017/0196478 A1 | 7/2017 | Hunter | |
| 2017/0196499 A1 | 7/2017 | Hunter | |
| 2017/0196508 A1 | 7/2017 | Hunter | |
| 2017/0196509 A1 | 7/2017 | Hunter | |
| 2018/0125365 A1 | 5/2018 | Hunter et al. | |
| 2018/0235546 A1 | 8/2018 | Hunter | |

FOREIGN PATENT DOCUMENTS

| | | |
|---|---|---|
| EP | 1814471 | 3/2010 |
| JP | 2005520630 | 7/2005 |
| JP | 2006055629 | 3/2006 |
| JP | 2007535372 | 12/2007 |
| JP | 2011514812 | 5/2011 |

(56) References Cited

FOREIGN PATENT DOCUMENTS

| | | |
|---|---|---|
| WO | 1997033513 | 9/1997 |
| WO | 2004016204 | 2/2004 |
| WO | 2004091419 | 10/2004 |
| WO | 2006105098 | 10/2006 |
| WO | 2008035089 | 3/2008 |
| WO | 2008152549 | 12/2008 |
| WO | 2009148847 | 12/2009 |
| WO | 2012061825 | 5/2012 |
| WO | 2013044160 | 3/2013 |
| WO | 2014053956 | 4/2014 |
| WO | 2014100795 | 6/2014 |
| WO | 2014130863 | 8/2014 |
| WO | 2015200704 | 6/2015 |
| WO | 2015200722 | 12/2015 |
| WO | 2016174612 | 11/2016 |
| WO | 2016180653 | 11/2016 |
| WO | 2016180654 | 11/2016 |
| WO | 2017165717 | 9/2017 |

OTHER PUBLICATIONS

International Search Report and Written Opinion for PCT/US2015/037803 dated Sep. 23, 2015.
PCT International Search Report and Written Opinion dated Jul. 7, 2014, for PCT/US2014/028381.
PCT International Search Report and Written Opinion dated Oct. 15, 2014, for PCT/US2014/043736.
PCT International Search Report and Written Opinion dated Feb. 1, 2016, for PCT/US2015/050789.
PCT International Search Report and Written Opinion dated Aug. 2, 2017, for PCT/US2017/023916.
European Partial Search Report dated Mar. 17, 2017, for 14762650.1.
European Partial Search Report dated Jun. 13, 2017, for 14817352.9.
European Partial Search Report dated Oct. 16, 2018 for 15842678.3.
European Full Extended Search Report dated Nov. 12, 2018 for 15812631.8.
European Extended Search Report dated Feb. 5, 2019 for 15842678.3.
Arami, Arash et al., "Instrumented Prosthesis for Knee Implant Monitoring", 2011 IEEE International Conference on Automation Science and Engineering, Trieste, Italy, Aug. 24-27, 2011, pp. 828-835.
Arami, Arash et al., "Accurate Measurement of Concurrent Flexion-Extension and Internal-External Rotations in Smart Knee Prostheses", IEEE Transactions on BioMedical Engineering, v. 60, No. 9, Sep. 2013, pp. 2504-2510.
Bosch Sensortec Data Sheet for BMI160 Small, low power inertial measurement unit, Doc Rev 0.8, Release Date Feb. 10, 2015, No. BST-BMI160-DS000-07, 110 pp.
Bosch for BMI160 Small, low power inertial measurement unit, Jan. 15, 2015, 2 pp.
Bosch Press Release, "Bosch Sensortec launches first IMU with sub 1mA current consumption", Jun. 25, 2014, 3 pp.
Ebrahim, A. F., et al., "The use of fiber Bragg grating sensors in biomechanics and rehabilitation applications: the state-of-the-art and ongoing research topics", Sensors, 2012, v 12, No. 10, pp. 12890-12929.
Forchelet, David et al. "Enclosed Electronic System for Force Measurements in Knee Implants", Sensors 2014, vol. 14, pp. 15009-15021.
Graichen, F., et al., "Hip endoprosthesis for in vivo measurement of joint force and termperative", Journal of Biomechanics, 1999, v 32, No. 10, pp. 1113-1117.
Heinlein, Bernd et al., "Design, calibration and pre-clinical testing of an instrumented tibial tray", Journal of Biomechanics, vol. 40, 2007, pp. S4-S10.
Jacq, Caroline et al., "Investigation of Polymer Thick-Film Piezoresistors for Medical Wristt Rehabilitation and Artificial Knee Load Sensors", Procedia Engineering, vol. 87, 2014, pp. 1194-1197.
Kroft, Steve, "The Data Brokers: Selling your Personal Information" pp. 1-8, extracted from Google on Sep. 4, 2014 is a script from "The Data Brokers" aired on Mar. 9, 2014 on 60 Minutes CBS.
Simoncini, Matteo; "Design and integration of an instrumented knee prosthesis", Thesis No. 6379 (2014), École Polytechnique Fédérale de Lausanne.

\* cited by examiner

DEVICES, SYSTEMS AND METHODS FOR USING AND MONITORING IMPLANTS

CROSS-REFERENCE TO RELATED APPLICATION

This application is a national phase application under 35 U.S.C. § 371 of International Application No. PCT/US2015/037803, filed Jun. 25, 2015, which claims the benefit under 35 U.S.C. § 119(e) of U.S. Provisional Patent Application No. 62/017,099, filed Jun. 25, 2014, which applications are incorporated herein by reference in their entirety.

FIELD OF THE INVENTION

The present invention relates generally to implants, and more specifically, to devices and methods for monitoring the placement, efficacy, and performance of implants, including for example, aesthetic implants.

BACKGROUND

Implantable prosthesis have been utilized to augment or replace tissue in humans for over a century. The first recorded description of a breast implant was by Vincenz Czerny in 1895, who moved a benign lipoma into a breast during reconstruction surgery in order to avoid asymmetry in the breast. Decades of experimentation with injectables (e.g., injection of paraffin wax, liquid silicone) and other materials (e.g., sponges and various plastics), let to poor results, including inflammation and infection, migration of the implant, embolization and granulation formation. However, in 1962 Frank Gerow and Thomas Cronin successfully implanted the first modern breast implant having a silicone shell containing a silicone gel.

Since that time implants have been utilized in a wide variety of aesthetic applications, including for example, facial (e.g., lips, chin, nasal, nasal/labial fold and malar implants), penile, and body contouring (e.g., breast, pectoral, calf, buttocks, abdomen and biceps/triceps) implants. However, despite their wide usage, implants are susceptible to a number of common complications.

For example, during a surgical procedure, the surgeon may wish to confirm correct anatomical alignment of the implant, symmetry with the implant on the contralateral side, and/or any motion between the implant and the surrounding tissue so that adjustments can be made during the procedure. Post-procedure, the patient may experience a large number of complications, including implant leakage or rupture, capsular contraction (i.e., the build-up of fibrous scar tissue around the implant, causing a contracture—hardening around the implant and apparent shrinkage of the implant itself), seromas and hematomas, inflammation, infection and pain. Over 20% of breast augmentations and 50% of breast reconstructions (implants placed after a previous mastectomy) will require explanation within 10 years for one or more of the above complications.

The present invention discloses novel implants which overcome many of the difficulties of previous implants, methods for constructing and monitoring these novel implants, and further provides other related advantages.

SUMMARY

Briefly stated, implants (also sometimes referred to as 'devices' or 'medical devices') are provided comprising an implant along with one or more sensors to monitor the integrity, position and efficaciousness of the implant. The sensors may be positioned on the inside of the implant, within the body of the implant, or on the outer surface (or surfaces) of the implant, and/or between the implant and any device that might be utilized to deliver the implant (e.g., another implant, catheter, tunneling catheter, endoscope, balloon implant, or other medical device). Within certain embodiments, the sensors are of the type that are passive and thus do not require their own power supply.

Representative examples of sensors suitable for use within the present invention include accelerometers (acceleration, tilt, vibration, shock and rotation sensors), pressure sensors, contact sensors, position sensors, chemical sensors, tissue metabolic sensors, mechanical stress sensors and temperature sensors. Within particularly preferred embodiments the sensor is a wireless sensor, or a sensor connected to a wireless microprocessor. Within further embodiments the implant or delivery device can have more than one type of the above-noted sensors.

According to various embodiments, sensors are placed at different locations in the implant in order to monitor the operation, movement, medical imaging (both of the implant and the surrounding tissues), function, wear, performance, potential side effects, medical status of the patient and the medical status of the implant and its interface with the live tissue of the patient. Live, continuous, in situ, monitoring of patient activity, patient function, implant activity, implant function, implant performance, implant placement, implant forces and mechanical stresses, implant and surrounding tissue anatomy (imaging), mechanical and physical integrity of the implant, and potential local and systemic side effects is provided. In addition, information is available on many aspects of the implant and its interaction with the patient's own body tissues, including clinically important measurements not currently available through physical examination, medical imaging and diagnostic medical studies.

According to one embodiment, the sensors provide evaluation data of any motion or movement of the implant. Motion sensors and accelerometers can be used to accurately determine the movement of the implant during surgical placement, during medical and physical examination post-operatively and during normal daily activities after the patient returns home.

Within further embodiments, the implant can contain sensors at specified densities in specific locations. For example, the implant can have a density of sensors of greater than one, two, three, four, five, six, seven, eight, nine, or ten sensors (e.g., accelerometers (acceleration, tilt, vibration, shock and rotation sensors), pressure sensors, contact sensors, position sensors, chemical sensors, tissue metabolic sensors, mechanical stress sensors and temperature sensors, or any combination of these) per square centimeter of the device/implant. Within other embodiments, the implant can have a density of sensors of greater than one, two, three, four, five, six, seven, eight, nine, or ten sensors (e.g., accelerometers (acceleration, tilt, vibration, shock and rotation sensors), pressure sensors, contact sensors, position sensors, chemical sensors, tissue metabolic sensors, mechanical stress sensors and temperature sensors, or any combination of these) per cubic centimeter of the device.

Within certain embodiments of the invention, the implant is provided with a specific unique identifying number, and within further embodiments, each of the sensors on, in or around the implant each have either a specific unique identification number, or a group identification number (e.g., an identification number that identifies the sensor as accelerometers (acceleration, tilt, vibration, shock and rotation sensors), pressure sensors, contact sensors, position sensors, chemical sensors, tissue metabolic sensors, mechanical stress sensors and temperature sensors). Within yet further embodiments, the specific unique identification number or group identification number is specifically associated with a position on, in or around the implant.

Within other aspects of the invention methods are provided for monitoring an implant comprising the steps of transmitting a wireless electrical signal from a location outside the body to a location inside the body; receiving the signal at a sensor positioned on, in or around an implant located inside the body; powering the sensor using the received signal; sensing data at the sensor; and outputting the sensed data from the sensor to a receiving unit located outside of the body.

Within other aspects of the invention methods are provided for imaging an implant as provided herein, comprising the steps of (a) detecting the location of one or more sensors in the implant, associated medical and/or associated medical delivery device or surgical tool; and (b) visually displaying the relative anatomical location (either surface or radiographic landmarks) of said one or more sensors, such that an image of the implant is created. Within various embodiments, the step of detecting may be done over time, and the visual display may thus show relative positional movement of the sensors and implant over time. Within certain preferred embodiments the image which is displayed is a three-dimensional image.

The imaging techniques provided herein may be utilized for a wide variety of purposes. For example, within one aspect, the imaging techniques may be utilized during a surgical procedure in order to ensure proper anatomical placement, bilaterally symmetry and functioning of the implant. Within other embodiments, the imaging techniques may be utilized post-operatively in order to examine the implant, and/or to compare operation, integrity and/or movement of the device/implant over time.

The integrity of the implant can be wirelessly interrogated and the results reported on a regular basis. This permits the health and status of the patient to be checked on a regular basis or at any time as desired by the patient and/or physician. Furthermore, the implant can be wirelessly interrogated when signaled by the patient to do so (via an external signaling/triggering device) as part of "event recording"—i.e. when the patient experiences a particular event (e.g. pain, injury, instability, etc.) she/he signals/triggers the device/implant to obtain a simultaneous reading in order to allow the comparison of subjective/symptomatic data to objective/sensor data. Matching event recording data with sensor data can be used as part of an effort to better understand the underlying cause or specific triggers of a patient's particular symptoms. Hence, within various embodiments of the invention methods are provided for detecting and/or recording an event in a subject with one of the implants provided herein, comprising the device/implant interrogation at a desired point in time. Within one aspect of the invention, methods are provided for detecting and/or recording an event in a subject with the implant as provided herein, comprising the step of interrogating at a desired point in time the activity of one or more sensors within the implant, and recording said activity. Within various embodiments, interrogation may be accomplished by the subject and/or by a health care professional. Within related embodiments, the step of recording may be performed with one or more wired devices, or, wireless devices that can be carried, or worn (e.g., a cellphone, watch or wristband, and/or glasses).

Within further embodiments, each of the sensors contains a signal-receiving circuit and a signal output circuit. The signal-receiving circuit receives an interrogation signal that includes both power and data collection request components. Using the power from the interrogation signal, the sensor powers up the parts of the circuitry needed to conduct the sensing, carries out the sensing, and then outputs the data to the interrogation module. The interrogation module acts under control of a control unit which contains the appropriate I/O circuitry, memory, a controller in the form of a microprocessor, and other circuitry in order to drive the interrogation module. Within yet other embodiments the sensors e.g., accelerometers (acceleration, tilt, vibration, shock and rotation sensors), pressure sensors, contact sensors, position sensors, chemical sensors, tissue metabolic sensors, mechanical stress sensors and temperature sensors are constructed such that they may readily be incorporated into, or otherwise mechanically attached to, the implant (e.g., by way of a an opening or other appendage that provides permanent attachment of the sensor to the implant) and/or readily incorporated into body of the implant.

Within yet other aspects of the invention methods, devices are provided suitable for transmitting a wireless electrical signal from a location outside the body to a location inside the body; receiving the signal at one of the aforementioned sensors positioned on, in or around the implant located inside the body; powering the sensor using the received signal; sensing data at the sensor; and outputting the sensed data from the sensor to a receiving unit located outside of the body. Within certain embodiments the receiving unit can provide an analysis of the signal provided by the sensor.

The data collected by the sensors can be stored in a memory located within the implant, or on an associated device (e.g., an associated medical device, or an external device such as a bra, cellphone, watch, wristband, and/or glasses. During a visit to the physician, the data can be downloaded via a wireless sensor, and the doctor is able to obtain data representative of real-time performance of the implant, and any associated medical device (e.g., a support bra).

The advantages obtained include more accurate monitoring of the implant and permitting medical reporting of accurate, in situ, data that will contribute to the health of the patient. The details of one or more embodiments are set forth in the description below. Other features, objects and advantages will be apparent from the description, the drawings, and the claims. In addition, the disclosures of all patents and patent applications referenced herein are incorporated by reference in their entirety.

DETAILED DESCRIPTION OF THE INVENTION

Figure 1A:
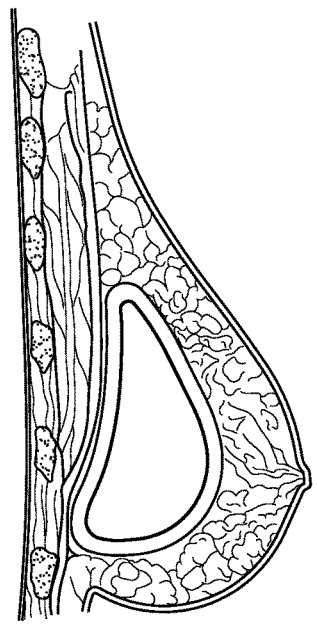
FIG. 1A illustrates the subglandular placement of a breast implant (i.e., between the breast tissue and the pectoralis major muscle).
Figure 1B:
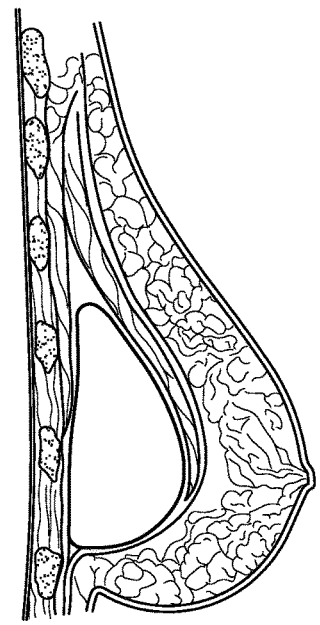
FIG. 1B illustrates the subfascial placement of a breast implant (i.e., beneath the fascia of the pectoralis major muscle and between the muscle and the chest wall).
Figure 2A:
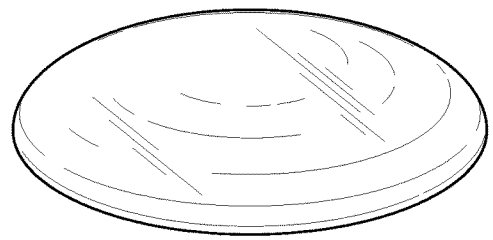
FIGS. 2A-C illustrate various breast implants, including a smooth implant (FIG. 2A), and two textured implants (FIG. 2B with a moderate contour, and FIG. 2C with a high contour).
Figure 2B:
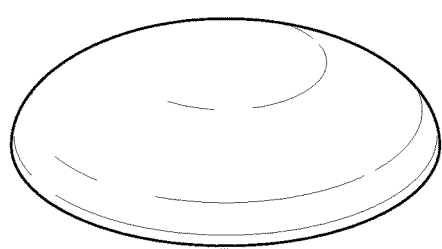
Figure 2C:
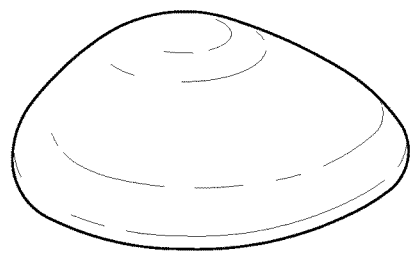

Briefly stated the present invention provides a variety of implants that can be utilized to monitor the placement, performance, integrity and/or efficaciousness of the implant. Prior to setting forth the invention however, it may be helpful to an understanding thereof to first set forth definitions of certain terms that are used hereinafter.

"Implant" as that term is utilized herein, refers to an artificial or synthetic prosthesis that has, or can be, implanted into a body. Implants are typically utilized to augment or replace a structure within the body, and have been utilized in a wide variety of aesthetic applications, including for example, for facial (e.g., lips, chin, nasal, nasal/labial fold and malar implants), penile, and body contouring (e.g., breast, pectoral, calf, buttocks, abdomen and biceps/triceps) implants.

"Surrounding Implant" as that term is utilized herein, refers to an artificial or synthetic implant or implanted material that is placed into the implant pocket where the aesthetic implant will ultimately be inserted. When an aesthetic implant is inserted into the body, a "pocket," or surgically created anatomical space, is first dissected into the tissue which will receive the aesthetic implant. A "surrounding implant" is typically a gel, adhesion barrier, hemostat, glue, and/or adhesive that is placed into the implant pocket such that it lies between the aesthetic implant and the host tissue (bags or other devices can placed around the aesthetic implant for the same purpose). Generally, the role of the "surrounding implant" is to prevent or minimize (at least initially) the contact between the aesthetic implant and the host tissue in an attempt to reduce scarring and capsular contraction.

Implants can be composed of a wide variety of materials, but utilizing breast implants as an example, they are typically comprised of an elastomeric outer surface or 'shell', and an interior 'filling'. With respect to the shell, silicone is the most commonly used elastomer, which may be either smooth, or textured. With respect to the filling, most implants are filled with either silicone, or saline (although other compositions have been suggested, including for example, peanut oil, sunflower oil, soy oil and polypropylene string).

Within various embodiments the implants may contain more than one internal filling (e.g., in different compartments), and may be coated (polymers, gels, drugs) and/or textured on the outer shell or provided with a bag in order to reduce the incidence of capsular contractions. In addition, implants can be provided in different sizes, and different shapes, and even customized to specific anatomical requirements. Within yet other embodiments one implant can be delivered to one location in the breast (e.g., subfascially), and another implant delivered to a different location (e.g., subglandularly).

Representative examples of implants are described in U.S. Pat. Nos. 4,995,882, 6,251,137, 6,464,726, 8,420,077 and U.S. Publication Nos. 2006/0136056, 2009/0099656, 2011/0184277, 2014/0088700. Representative examples of implant delivery devices include U.S. Pat. No. 8,550,090 and U.S. Publication Nos. 2014/0074235, and 2014/0074236.

The implants and medical devices provided herein are preferably sterile, non-pyrogenic, and/or suitable for use and/or implantation into humans. However, within certain embodiments of the invention the medical devices and/or kits may be made in a non-sterilized environment (or even customized or "printed" for an individual subject), and sterilized at a later point in time.

"Sensor" refers to a device that can be utilized to measure one or more different aspects of a body tissue (anatomy, physiology, metabolism, and/or function), one or more aspects of the implant, one or more aspects of a surrounding implant (e.g. barriers, gels, adhesives, etc.) placed into the implant pocket, and/or one or more aspects of any associated delivery devices. Representative examples of sensors suitable for use within the present invention include, for example, fluid pressure sensors, fluid volume sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors and temperature sensors. Within certain embodiments the sensor can be a wireless sensor, or, within other embodiments, a sensor connected to a wireless microprocessor. Within further embodiments one or more (including all) of the sensors can have a Unique Sensor Identification number ("USI") which specifically identifies the sensor.

A wide variety of sensors (also referred to as Microelectromechanical Systems or "MEMS", or Nanoelectromechanical Systems or "NEMS", and BioMEMS or BioNEMS, see generally https://en.wikipedia.org/wiki/MEMS) can be utilized within the present invention. Representative patents and patent applications include U.S. Pat. Nos. 7,383,071, 7,450,332; 7,463,997, 7,924,267 and 8,634,928, and U.S. Publication Nos. 2010/0285082, and 2013/0215979. Representative publications include "Introduction to BioMEMS" by Albert Foch, CRC Press, 2013; "From MEMS to Bio-MEMS and Bio-NEMS: Manufacturing Techniques and Applications by Marc J. Madou, CRC Press 2011; "Bio-MEMS: Science and Engineering Perspectives, by Simona Badilescu, CRC Press 2011; "Fundamentals of BioMEMS and Medical Microdevices" by Steven S. Saliterman, SPIE—The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations," *J. Microelectromechanical Sys.*, 11:5, October 2002, 454-461; Yeh, R., et al., "Single Mask, Large Force, and Large Displacement Electrostatic Linear Inchworm Motors," *J. Microelectromechanical Sys.*, 11:4, August 2002, 330-336; and Loh, N. C., et al., "Sub-10 $cm^3$ Interferometric Accelerometer with Nano-g Resolution," *J. Microelectromechanical Sys.*, 11:3, June 2002, 182-187; all of the above of which are incorporated by reference in their entirety.

Within various embodiments of the invention the sensors described herein may be placed at a variety of locations and in a variety of configurations, on the inside (i.e. in the "filling") of the implant, within the body of the implant shell, on the outer surface of the implant shell, on the inner surface of the implant shell, and/or on, within or outside of any surrounding implant (e.g., a gel, adhesion barrier, hemostat, glue, and/or adhesive placed in the implant pocket; and/or a bag or other device placed around the aesthetic implant), as well as between the implant and any device that might carry or deliver it (e.g., a delivery device or surgical instrument). Within certain embodiments, the implant, surrounding implant, and/or delivery device comprises sensors at a density of greater than 1, 2, 3, 4, 5, 6, 7, 8, 9, 10 or greater than 10 sensors per square centimeter. Within other aspects, the implant, surrounding implant, and/or delivery device comprises sensors at a density of greater than 1, 2, 3, 4, 5, 6, 7, 8, 9, 10 or greater than 10 sensors per cubic centimeter. Within either of these embodiments, there can be less than 50, 75, 100, or 100 sensors per square centimeter, or per cubic centimeter. Within various embodiments, at least one or more of the sensors may be placed randomly, or at one or more specific locations within the implant, surrounding implant and/or delivery device as described herein.

In various embodiments, the sensors may be placed within specific locations and/or randomly throughout the implant, surrounding implant and/or associated devices. In addition, the sensors may be placed in specific patterns (e.g., they may be arranged in the pattern of an X, as oval or concentric rings around the implant, surrounding implant, and/or associated devices.

Representative Embodiments of Implants and Medical Uses of Sensor-Containing Implants In order to further understand the various aspects of the invention provided herein, the following sections are provided below: A. Implants and their Use; B. Use of Implants to Deliver Therapeutic Agent(s); C. Methods for Monitoring Infection in Implants; D. Further Uses of Sensor-containing Implants in Healthcare; E. Generation of Power from Implants; F. Medical Imaging and Self-Diagnosis of Assemblies Comprising Implants, Predictive Analysis and Predictive Maintenance; G. Methods of Monitoring Assemblies Comprising Implants; and H. Collection, Transmission, Analysis, and Distribution of Data from Assemblies Comprising Implants.

A. Implants and their Use

Figure 3:
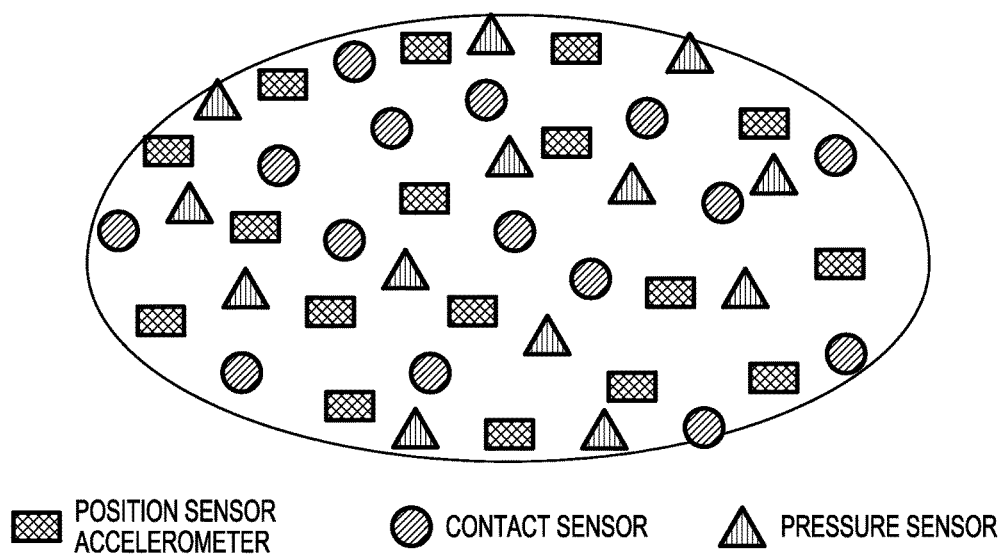
FIG. 3 illustrates one embodiment wherein sensors of various types are deployed on the surface of an implant.

As noted above, the present invention provides implants which comprise one or more sensors. For example, as shown in FIG. 3, implants are provided comprising a variety of sensors. Within one embodiment one or more position sensors and/or accelerometers are placed within the 'filling', or on or within the 'shell' of an implant. Such sensors are capable of providing: a) an image of the implant (or 'real-time' imaging of the implant); b) assistance during placement of the implant, and confirmation subsequent to implant of the correct anatomical location (e.g., by way of the aforementioned imaging, or by comparison with external markers); and c) confirmation of full inflation (i.e. not folded or wrinkled in situ). In addition, such sensors are useful in confirming that the implant is operating as expected [e.g., a) confirming that it has not moved or migrated; b) confirming that scarring or capsular contraction has not begun; c) confirming that the integrity of the implant is sound (i.e., that there are no leaks) as determined from within the implant, or by determination of a leak from the surface of the implant; and d) confirming that the implant is not wrinkled or folded]. Sensors can also be utilized to ensure that acute complications are not developing (e.g., the development of a hematoma, seroma, granuloma, abscess, or other mass in the tissues surrounding the implant that applies external pressure to the implant itself).

Within other embodiments, implants are provided with one or more contact sensors and/or pressure sensors. As noted above, the contact and/or pressure sensors can be placed within the 'filling', or, on or within the 'shell' of the implant. Such sensors are capable of providing: a) an image of the implant (or 'real-time' imaging of the implant); b) assistance during placement of the implant, and confirmation subsequent to implant of the correct anatomical location (e.g., by way of the aforementioned imaging, or by comparison with external markers); and c) confirmation of full inflation (i.e. not folded or wrinkled in situ). In addition, such sensors are useful in confirming that the implant is operating as expected [e.g., a) confirming that it has not moved or migrated; b) confirming that scarring or capsular contraction has not begun; and c) confirming that the integrity of the implant is sound (i.e., that there are no leaks) as determined from within the implant, or by determination of a leak from the surface of the implant; and d) confirming that the implant is not wrinkled or folded]. Sensors can also be utilized to ensure that acute complications are not developing (e.g., the development of a hematoma, seroma, granuloma, abscess, or other mass in the tissues surrounding the implant that applies external pressure to the implant itself).

Within yet other embodiments implants are provided with one or more accelerometers. Such accelerometers can be utilized to a) determine the durability of the implant based upon 'real-world' conditions; b) determine if different implants are better in certain patients (based upon activity levels, impact, forces, weight, etc.); and c) assist manufacturers in the design of new implants, product improvements, and collection of clinical data. Moreover, it would allow the evaluation of performance of different devices under similar conditions, and the ability of the patient to monitor their progress at home.

Within other embodiments implants are provided with one or more temperature sensors and/or chemical or metabolic sensors. Such sensors can be utilized to detect the presence of infection, seroma, hematoma and inflammation and allow for rapid or preemptive intervention (e.g., administration of antibiotics before a full-blown infection has developed, drainage of a subclinical hematoma or seroma, or undertake measures to reduce inflammation in an effort to lower the chance of a capsular contracture developing).

It should be obvious to one of skill in the art that the same sensors can be incorporated into a surrounding implant for the same purposes as described above.

As will be evident given the disclosure provided herein, a wide variety of other sensors may also be utilized within, or on the implant, including for example, pulse pressure sensors, heart rate sensors, glucose sensors, or sensors to detect tumor (particularly breast cancer) markers.

Within various embodiments any of the aforementioned sensors can be provided at a density of greater than 1, 2, 3, 4, 5, 6, 7, 8, 9, 10 or 20 sensors per square centimeter; and or sensors a density of greater than 1, 2, 3, 4, 5, 6, 7, 8, 9, 10 or 20 sensors per cubic centimeter.

Within various embodiments of the invention, methods are also provided for manufacturing an implant having one of the sensors provided herein. For example, within one embodiment of the invention an implant (e.g., for facial (e.g., lips, chin, nasal, nasal/labial fold and malar implants), penile, or body contouring (e.g., breast, pectoral, calf, buttocks, abdomen and biceps/triceps) is constructed such that one or more sensors provided herein are placed directly into the implant at the time of manufacture, and subsequently sterilized in a manner suitable for use in subjects.

Within further embodiments, the present disclosure provides a method of making an implant by 3D printing, additive manufacturing, or a similar process whereby the implant is formed from powder or filament that is converted to a fluid form such subsequently solidifies as the desired shape. For convenience, such processes will be referred to herein as printing processes or 3D printing processes. The present disclosure provide a method of making an implant by a printing process, where that implant includes a sensor, circuit or other feature as disclosed herein (collectively sensor or sensors). The sensor may be separately produced and then incorporated into the implant during the printing process. For example, a sensor may be placed into a desired position and the printing process is carried out around the sensor so that the sensor becomes embedded in the printed implant. Alternatively, the printing process may be started and then at appropriate times, the process is paused to allow a sensor to be placed adjacent to the partially completed implant. The printing process is then re-started and construction of the implant is completed. The software that directs the printing process may be programmed to pause at appropriate predetermined times to allow a sensor to be added to the partially printed implant.

In addition, or alternatively, the sensor itself, or a portion thereof may be printed by the 3D printing process. Likewise, electronic connectively to, or from, or between, sensors may be printed by the 3D printing process. For example, conductive silver inks may be deposited during the printing process to thereby allow conductivity to, or from, or between sensors of an implant. See, e.g., PCT publication nos. WO 2014/085170; WO 2013/096664; WO 2011/126706; and WO 2010/0040034 and US publication nos. US 2011/0059234; and US 2010/0037731. Thus, in various embodiments, the present disclosure provides implants wherein the sensor is printed onto a substrate, or a substrate is printed and a sensor is embedded or otherwise incorporated into or onto the substrate, or both the substrate and the sensor are printed by a 3D printing technique.

3D printing may be performed using various printing materials, typically delivered to the 3D printer in the form of a filament. Two common printing materials are polylactic acid (PLA) and acrylonitrile-butadiene-styrene (ABS), each being an example of a thermoplastic polymer. When strength and/or temperature resistance is particularly desirable, then polycarbonate (PC) may be used as the printing material. Other polymers may also be used. See, e.g., PCT publication nos. WO 2014/081594 for a disclosure of polyamide printing material. When metal parts are desired, a filament may be prepared from metal or metal alloy, along with a carrier material which ultimately will be washed or burned or otherwise removed from the part after the metal or metal alloy has been delivered.

When the implant is of a particularly intricate shape, it may be printed with two materials. The first material is cured (using, e.g., actinic radiation) as it is deposited, while the second material is uncured and can be washed away after the implant has been finally printed. In this way, significant hollow spaces may be incorporated into the implant.

Additive manufacturing is a term sometimes used to encompass printing techniques wherein metal or metal allow is the material from which the desired part is made. Such additive manufacturing processes utilizes lasers and build an object by adding ultrathin layers of materials one by one. For example, a computer-controlled laser may be used to direct pinpoint beams of energy onto a bed of cobalt-chromium alloy powder, thereby melting the alloy in the desired area and creating a 10-30-micron thick layer. Adjacent layers are sequentially and repetitively produced to create the desired sized item. As needed, a sensor may be embedded into the alloy powder bed, and the laser melts the powder around the sensor so as to incorporate the sensor into the final product. Other alloys, including titanium, aluminum, and nickel-chromium alloys, may also be used in the additive manufacturing process. See, e.g., PCT publication nos. WO 2014/083277; WO 2014/074947; WO 2014/071968; and WO 2014/071135; as well as US publication nos. US 2014/077421; and US 2014/053956.

Accordingly, in one embodiment the present disclosure provides a method of fabricating a sensor-containing implant, the method comprising forming at least one of a sensor and a support for the sensor using a 3D printing technique. Optionally, the 3D printing technique may be an additive manufacturing technique. In a related embodiment, the present disclosure provides an implant that is produced by a process comprising a 3D printing process, such as an additive manufacturing process, where the implant includes a sensor.

Within yet further embodiments of the invention, the implant may be filled subsequent to manufacture (e.g., in the case of a breast implant) and/or sterilized suitable for use in a subject.

Disclosure of 3D printing processes and/or additive manufacturing is found in, for example PCT publication nos. WO 2014/020085; WO 2014/018100; WO 2013/179017; WO 2013/163585; WO 2013/155500; WO 2013/152805; WO 2013/152751; WO 2013/140147 and US publication nos. 2014/048970; 2014/034626; US 2013/337256; 2013/329258; US 2013/270750.

B. Use of Implants to Deliver Therapeutic Agent(s)

As noted above, the present invention also provides drug-eluting implants, drug-coated implants and/or drug-eluting surrounding implants which comprise one or more sensors, and which can be utilized to release a therapeutic agent (e.g., a drug) to a desired location within the body (e.g., a body tissue). Within related embodiments, a drug-eluting delivery device may be included within the implant and/or surrounding implant in order to release a desired drug upon demand (e.g., upon remote activation/demand, or based upon a timed schedule), or upon detection of an activating event (e.g., detection of an accelerometer of a significant impact event, or detection of loosening by a contact sensor) (see generally U.S. Patent App. No. 2011/0092948 entitled "Remotely Activated Piezoelectric Pump For Delivery of Biological Agents to the Intervertebral Disc and Spine", which is incorporated by reference in its entirety).

For example, within certain embodiments of the invention, biological agents can be administered along with or released from a implant and/or surrounding implant in order to decrease the likelihood of capsular contraction, or to reduce or inhibit the occurrence of scaring or fibrosis in or around the implant (see, e.g., U.S. Pat. No. 7,491,188, U.S. Patent Application Nos. 2005/0152945, 2005/0187639, 2006/0079836, US 2009/0254063, US 2010/0023108, and US 2010/0042121).

Within other embodiments of the invention, anti-inflammatory agents, local anesthetics and pain-relief medications (e.g., drugs such as cortisone, dexamethasone, nonsteroidal anti-inflammatories, lidocaine, marcaine, morphine, codeine, narcotic pain relievers and analogs or derivatives of these) can be utilized to reduce post-operative pain and swelling and reduce the need for systemic pain relief therapy.

Within other embodiments a wide variety of additional therapeutic agents may be delivered (e.g., to prevent or treat an infection or to treat another disease state), including for example: Anthracyclines (e.g., gentamycin, tobramycin, doxorubicin and mitoxantrone); Fluoropyrimidines (e.g., 5-FU); Folic acid antagonists (e.g., methotrexate); Podophylotoxins (e.g., etoposide); Camptothecins; Hydroxyureas, and Platinum complexes (e.g., cisplatin) (see e.g., U.S. Pat. No. 8,372,420 which is incorporated by reference in its entirety. Other therapeutic agents include beta-lactam antibiotics (e.g., the penicillins, cephalosporins, carbacephems and carbapenems); aminoglycosides (e.g., sulfonamides, quinolones and the oxazolidinones); glycopeptides (e.g., vancomycin); lincosamides (e.g., clindamycin); lipopeptides; macrolides (e.g., azithromycin); monobactams; nitrofurans; polypeptides (e.g., bacitracin); and tetracyclines.

Within preferred embodiments one or more sensors (e.g., pressure sensors, contact sensors, and/or position sensors) can be utilized to determine appropriate placement of the desired drug, as well as the quantity and release kinetics of drug to be released at a desired site.

C. Methods for Monitoring Infection

Within other embodiments implants are provided comprising one or more temperature sensors, pH sensors, chemical sensors and biological sensors. Such implants can be utilized to measure the temperature of the implant, and in the local tissue adjacent to the implant. Methods are also provided for monitoring changes in temperature over time, in order to determine and/or provide notice (e.g., to a patient and/or a healthcare provider) that an infection may be imminent. Methods are provided for monitoring other indicators of infection such as pH, metabolic levels (e.g. oxygen and $CO_2$ content), and/or biological agents (sensors able to detect specific species of bacteria or bacterial DNA). For example, temperature sensors, pH sensors, metabolic sensors, and/or biologic sensors may be included within one or more parts of the implant (e.g., on or within the shell, or within the filling) and/or a surrounding implant in order to allow early detection of infection that could allow preemptive treatment with antibiotics, tissue lavage, and/or surgical drainage (and potentially eliminate the need to surgically remove the implant).

Hence, within one embodiment of the invention methods are provided for determining an infection associated with an implant, comprising the steps of a) providing to a subject an implant and/or surrounding implant as described herein, wherein the implant and/or surrounding implant comprises at least one temperature sensor and/or metabolic sensor, and b) detecting a change in said temperature sensor and/or metabolic sensor, and thus determining the presence of an infection. Within various embodiments of the invention the step of detecting may be a series of detections over time, and a change in the sensor is utilized to assess the presence or development of an infection. Within further embodiments a change of 0.5%, 1.0%, or 1.5% elevation of temperature or a metabolic factor over time (e.g., 0.5, 1.0, 1.5, 2.0, 2.5, 3.0, 3.5, 4 hours, 12 hours, 1 day, or 2 days) can be indicative of the presence of an infection (or a developing infection).

Within various embodiments of the invention an antibiotic may be delivered in order to prevent, inhibit or treat an infection subsequent to its detection. Representative examples of suitable antibiotics are well known, and are described above under Section B (the "Therapeutic Agents")

D. Further Uses of Sensor-Containing Implants in Healthcare

Sensors on implants have a variety of benefits in the healthcare setting, and in non-healthcare settings (e.g., at home or work). For example, postoperative progress can be monitored (readings compared from day-to-day, week-to-week, etc.) and the information compiled and relayed to both the patient and the attending physician allowing rehabilitation to be followed sequentially and compared to expected (typical population) norms. Within certain embodiments, a wearable device interrogates the sensors on a selected or randomized basis, and captures and/or stores the collected sensor data. This data may then be downloaded to another system or device (as described in further detail below).

Integrating the data collected by the sensors described herein (e.g., contact sensors, position sensors, volume sensors, strain gauges and/or accelerometers) with simple, widely available, commercial analytical technologies such as pedometers and global positioning satellite (GPS) capability, allows further clinically important data to be collected such as, but not restricted to: extent of patient ambulation (time, distance, steps, speed, cadence), patient activity levels (frequency of activity, duration, intensity), exercise tolerance (work, calories, power, training effect), range of motion and implant performance under various "real world" conditions. It is difficult to overstate the value of this information in enabling better management of the patient's recovery. An attending physician (or physiotherapist, rehabilitation specialist) only observes the patient episodically during scheduled visits; the degree of patient function at the exact moment of examination can be impacted by a multitude of disparate factors such as: the presence or absence of pain, the presence or absence of inflammation, time of day, compliance and timing of medication use (pain medications, anti-inflammatories), recent activity, patient strength, mental status, language barriers, the nature of their doctor-patient relationship, or even the patient's ability to accurately articulate their symptoms—to name just a few. Continuous monitoring and data collection can allow the patient and the physician to monitor progress objectively by supplying objective information about patient function under numerous conditions and circumstances, to evaluate how performance has been affected by various interventions (pain control, anti-inflammatory medication, rest, etc.), and to compare patient progress versus previous function and future expected function. Better therapeutic decisions and better patient compliance can be expected when both the doctor and the patient have the benefit of observing the impact of various treatment modalities on patient rehabilitation, activity, function and overall performance.

E. Generation of Power

Within certain aspects of the invention, a small electrical generation unit can be positioned along an outer, or alternatively an inner, surface of the implant. Briefly, a variety of techniques have been described for scavenging power from small mechanical movements or mechanical vibration. See, for example, the article entitled "Piezoelectric Power Scavenging of Mechanical Vibration Energy," by U.K. Singh et al., as published in the Australian Mining Technology Conference, Oct. 2-4, 2007, pp. 111-118, and the article entitled "Next Generation Micro-power Systems by Chandrakasan et al., as published in the 2008 Symposium on VLSI Circuits Digest of Technical Papers, pp. 1-5. See also U.S. Pat. No. 8,283,793 entitled "Device for Energy Harvesting within a Vessel," and U.S. Pat. No. 8,311,632 entitled "Devices, Methods and Systems for Harvesting Energy in the Body," all of the above of which are incorporated by reference in their entirety. These references provide examples of different types of power scavengers which can produce electricity from very small motion and store the electricity for later use. The above references also describes embodiments in which pressure is applied and released from the particular structure in order to produce electricity without the need for motion, but rather as a result of the application of high pressure. In addition, these references describe embodiments wherein electricity can be produced from pulsatile forces within the body and movements within the body.

Figure 4:
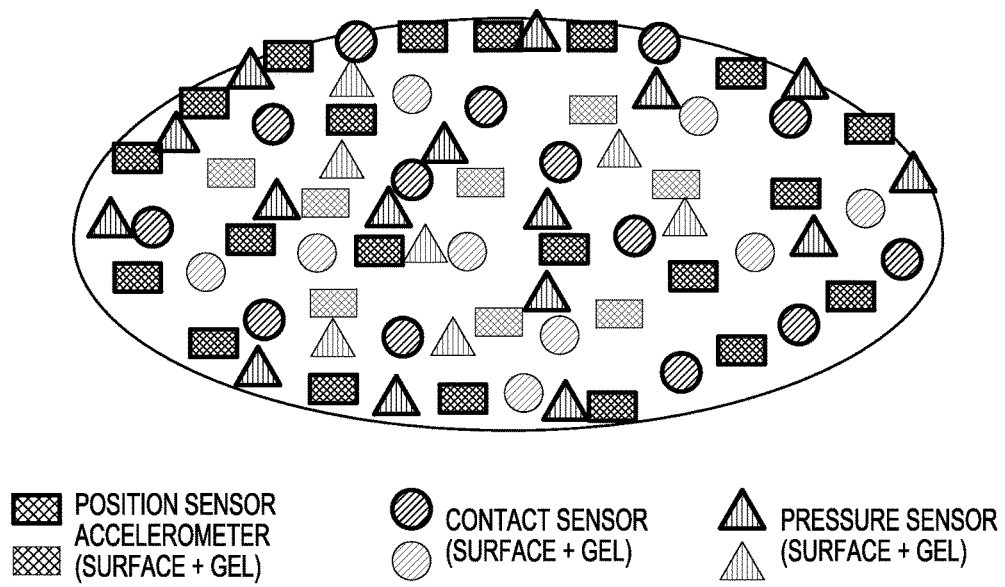
FIG. 4 illustrates one embodiment wherein sensors of various types are deployed on the surface (bordered boxes squares and triangles) and within the interior (non-bordered boxes, circles and triangles).
Figure 5:
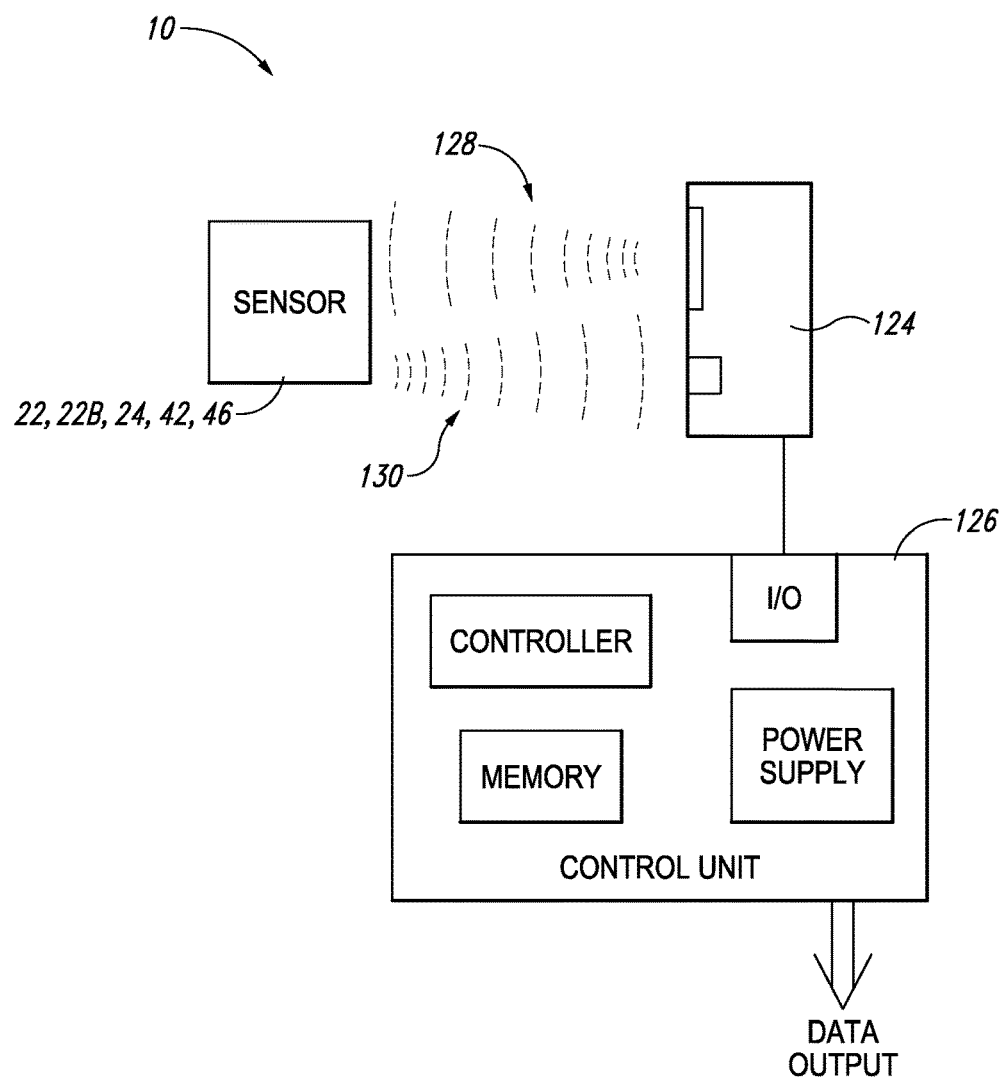
FIG. 5 illustrates an information and communication technology system embodiment arranged to process sensor data.

After the electricity is generated by one or more generators, the electricity can be transmitted to any one of the variety of sensors which is described herein. For example, it can be transmitted to any of the sensors shown in FIGS. 3 and 4. It may also be transmitted to the other sensors described herein. The transmission of the power can be carried out by any acceptable technique. For example, if the sensor is physically coupled to the implant, electric wires may run from the generator to the particular sensor. Alternatively, the electricity can be transmitted wirelessly in the same way that wireless smartcards receive power from closely adjacent power sources using the appropriate send and receive antennas. Such send and receive techniques of electric power are also described in the publication and the patent applications and issued U.S. patent previously described, all of which are incorporated herein by reference.

F. Medical Imaging and Self-Diagnosis of Assemblies Comprising Implants; Predictive Analysis and Predictive Maintenance Within other aspects of the invention methods are provided for imaging the implant as provided herein, comprising the steps of (a) detecting the location of one or more sensors in the implant; and (b) visually displaying the location of said one or more sensors, such that an image of the implant and/or surrounding implant is created. Within various embodiments, the step of detecting may be done over time, and the visual display may thus show positional movement over time. Within certain preferred embodiments the image which is displayed is a three-dimensional image. Within preferred embodiments the various images may be collected and displayed in a time-sequence (e.g., as a 2D or 3D moving image or 'movie-like' image). Within other embodiment, the imaging techniques may be utilized post-operatively in order to examine the implant, and/or to compare operation and/or movement of the device over time.

The present invention provides implants, surrounding implants and associated medical devices (e.g., delivery devices and support wear, such as support bras) which are capable of imaging through the use of sensors over a wide variety of conditions. For example, within various aspects of the invention, methods are provided for imaging the implant (or portion thereof) or an assembly comprising the implant, surrounding implant and/or delivery device (as described herein) with sensors, comprising the steps of detecting the changes in sensors in, on, and or within the implant, surrounding implant and/or delivery device over time, and wherein the implant, surrounding implant and/or delivery device comprises sensors at a density of greater than 1, 2, 3, 4, 5, 6, 7, 8, 9, 10 or greater than 10 sensors per square centimeter. Within other aspects the implant medical device or kit comprises sensors at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter. Within various embodiments, at least one or more of the sensors may be placed randomly, or at one or more specific locations within the implant, surrounding implant and/or delivery device as described herein. As noted above, a wide variety of sensors can be utilized therein, including for example, contact sensors, strain gauge sensors, pressure sensors, fluid pressure sensors, position sensors, tissue chemistry sensors, tissue metabolic sensors, mechanical stress sensors, and temperature sensors.

For example, the implant, surrounding implant and/or delivery device comprising sensors as described herein can be utilized to image anatomy through sensors which can detect positional movement. The sensors used can also include accelerometers and motion sensors to detect movement of the implant due to a variety of physical changes. Changes in the position of the accelerometers and/or motion sensors over time can be used as a measurement of changes in the position of the implant over time. Such positional changes can be used as a surrogate marker of implant anatomy—i.e. they can form an "image' of the implant to provide information on the size, shape, integrity, alignment and location of changes to the implant, and/or implant movement/migration. In particular, as noted above, the image data can be collected over time, in order to visually show changes (e.g., a "movie" or 'moving images", which may be in 2D or 3D).

Figure 6:
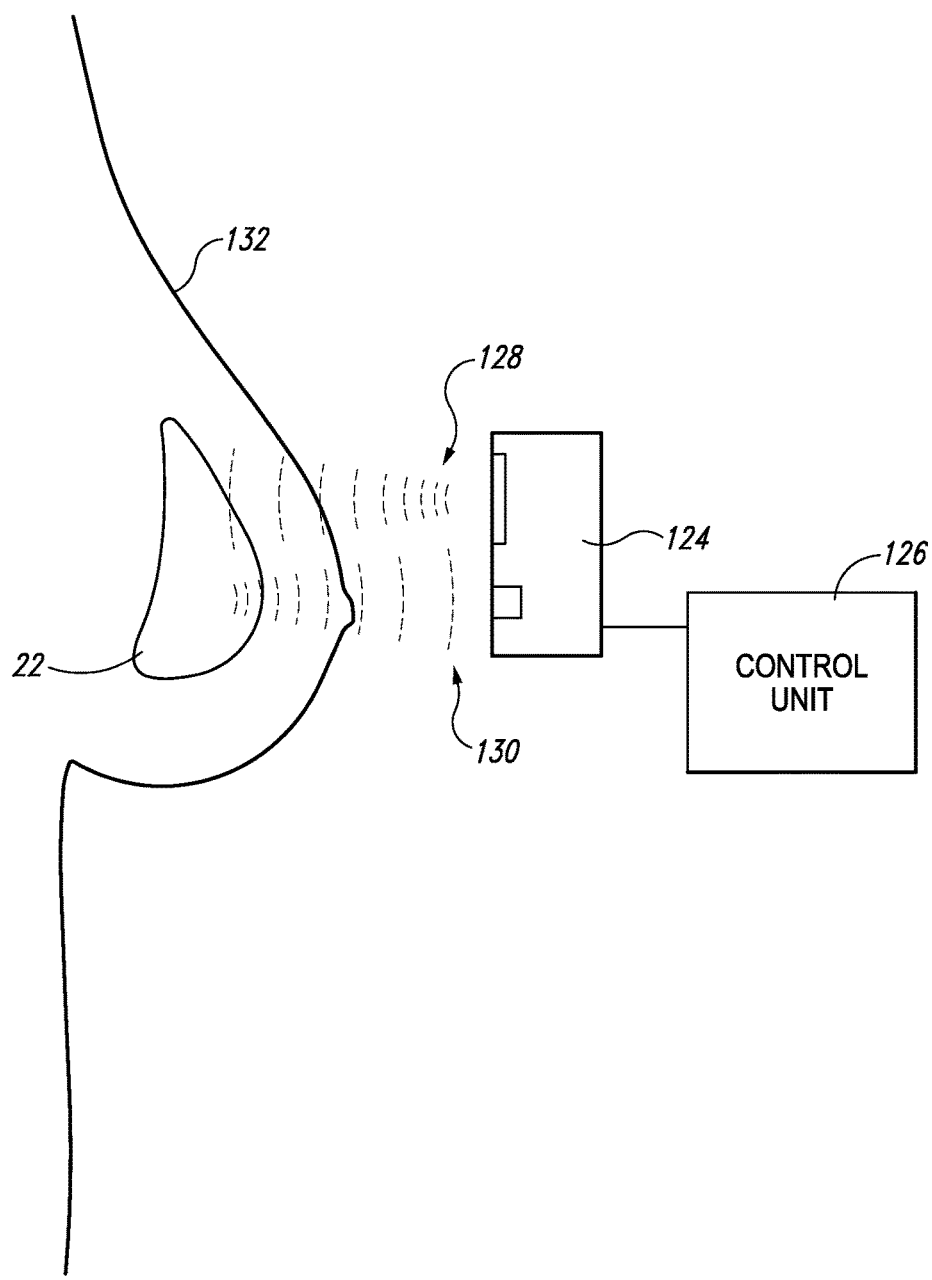
FIG. 6 is a block diagram of a sensor, interrogation module, and a control unit according to one embodiment of the invention.

Certain exemplary embodiments will now be explained in more detail. One particular benefit is the live and in-situ monitoring of the patient's recovery with an implant having sensor 22 as shown in FIG. 6. The sensors as described herein are collecting data on a constant basis, during normal daily activities and even during the night if desired. For example, the contact sensors can obtain and report data once every 10 seconds, once a minute, or once a day. Other sensors will collect data more frequently, such as several times a second. For example, it would be expected that the temperature, contact, and/or position data could be collected and stored several times a second. Other types of data might only need to be collected by the minute or by the hour. Still other sensors may collect data only when signaled by the patient to do so (via an external signaling/triggering device) as part of "event recording"—i.e. when the patient experiences a particular event (e.g. pain, injury, etc.)—and signals the device to obtain a reading at that time in order to allow the comparison of subjective/symptomatic data to objective/sensor data in an effort to better understand the underlying cause or triggers of the patient's symptoms.

In certain instances the implant is of sufficient size and has more than sufficient space in order to house one or more processor circuits, CPUs, memory chips and other electrical circuits as well as antennas for sending and receiving the data. Within other embodiments, an associated medical device (e.g., delivery device, or external wearable support) may be able to house the one or more processor circuits, CPUs, memory chips and other electrical circuits as well as antennas for sending and receiving the data. Processors can be programmed to collect data from the various sensors on any desired schedule as set by the medical professional. All activity can be continuously monitored post operation or post-procedure and the data collected and stored in the memory located inside the implant.

A patient with an implant will generally have regular medical checkups. When the patient goes to the doctor's office for a medical checkup, the doctor will bring a reading device closely adjacent to the implant 10, in this example the implant, in order to transfer the data from the internal circuit inside the implant to the database in the physician's office. The use of wireless transmission using smartcards or other techniques is very well known in the art and need not be described in detail. Examples of such wireless transmission of data are provided in the published patent applications and patents which have been described herein. The data which has been collected (e.g., over a short period of time, over several weeks or even several months) is transferred in a few moments from the memory which is positioned in the implant to the doctor's computer or wireless device. The computer therefore analyzes the data for anomalies, unexpected changes over time, positive or negative trends, and other signs which may be indicative of the health of the patient and the operability of the implant. For example, if the patient has decided to go skiing or jogging, the doctor will be able to monitor the effect of such activity on the implant 10, including the accelerations and strains during the event itself. The doctor can then look at the health of the implant in the hours and days after the event and compare it to data prior to the event to determine if any particular event caused long term damage, or if the activities subjected the implant to forces beyond the manufacturer's performance specifications for that particular implant. Data can be collected and compared with respect to the ongoing and long term performance of the implant from the strain gauges, the contact sensors, the surface wear sensors, or other sensors which may be present. Hence, within preferred embodiments the data can be collected over time, in order to visually show changes (e.g., a 2D or 3D "movie" or 'moving images").

In one alternative, the patient may also have such a reading device in their home which collates the data from the implant on a periodic basis, such as once per day or once per week. As described above, the patient may also be able to "trigger" a device reading (via an external signaling/triggering device) as part of "event recording." For example, within certain embodiments the devices and systems provided herein can instruct or otherwise notify the patient, or a permitted third-party as to deviations (e.g., greater than 10%, 20%, 25%, 50%, 70%, and or 100%) from normal, and/or, set parameters. Empowering the patient to follow their own rehabilitation—and enabling them to see the positive (and negative) effects of various lifestyle choices on their health and rehabilitation—can be expected to improve compliance and improve patient outcomes. Furthermore, their experience can be shared via the web with other patients to compare their progress versus expected "norms" for function and rehabilitation and alert them to signs and symptoms that should be brought to their doctor's attention. The performance of different implants can be compared in different patients (different sexes, weights, activity levels, etc.) to help manufacturers design better devices and assist surgeons and other healthcare providers in the selection of the right implant for specific patient types. Payers, patients, manufacturers and physicians could all benefit from the collection of this comparative information. Lastly, data accumulated at home can be collected and transmitted via the Internet to the physician's office for analysis—potentially eliminating unnecessary visits in some cases and encouraging immediate medical follow-up in others.

G. Methods of Monitoring Assemblies Comprising Implants

As noted above, the present invention also provides methods for monitoring one or more of the implants provided herein. For example, FIG. 6 illustrates a monitoring system usable with the implant as of the type shown in any one of the Figures described above. The monitoring system includes one or more sensors 22 an interrogation module 124, and a control unit 126. The sensor 22 can be passive, wireless type which can operate on power received from a wireless source. Such sensors of this type are well known in the art and widely available. A pressure sensor of this type might be a MEMS pressure sensor, for example, Part No. LPS331AP, sold on the open market by STMicroelectronics. MEMS pressure sensors are well known to operate on very low power and suitable to remain unpowered and idle for long periods of time. They can be provided power wirelessly on an RF signal and, based on the power received wirelessly on the RF signal, perform the pressure sensing and then output the sensed data.

In one embodiment, an electrical generation system (as described above) is provided that can be utilized to power the sensors described herein. During operation, as shown in FIG. 20, an interrogation module 124 outputs a signal 128. The signal 128 is a wireless signal, usually in the RF band, that contains power for the sensors 22 as well as an interrogation request that the sensors perform a sensing. Upon being interrogated with the signal 128, the sensors 22 powers up and stores power in onboard capacitors sufficient to maintain operation during the sensing and data reporting. Such power receiving circuits and storing on onboard capacitors are well known in the art and therefore need not be shown in detail. The appropriate sensing is carried out by the sensors 22 and then the data is output from the sensor back to the interrogation module 124 on a signal 130, where it is received at an input port of the integration module.

According to one embodiment, sufficient signal strength is provided in the initial signal 128 to provide power for the sensor and to carry out the sensing operation and output the signal back to the interrogation module 124. In other embodiments, two or more signals 128 are sent, each signal providing additional power to the sensor to permit it to complete the sensing operation and then provide sufficient power to transfer the data via the signal path 130 back to the interrogation module 124. For example, the signal 128 can be sent continuously, with a sensing request component at the first part of the signal and then continued providing, either as a steady signal or pulses to provide power to operate the sensor. When the sensor is ready to output the data, it sends a signal alerting the interrogation module 124 that data is coming and the signal 128 can be turned off to avoid interference. Alternatively, the integration signal 128 can be at a first frequency and the output signal 130 at a second frequency separated sufficiently that they do not interfere with each other. In a preferred embodiment, they are both the same frequency so that the same antenna on the sensor can receive the signal 128 and send signal 130.

The interrogation signal 128 may contain data to select specific sensors on the implant. For example, the signal 128 may power up all sensors on the implant at the same time and then send requests for data from each at different selected times so that with one interrogation signal 128 provided for a set time, such as 1-2 seconds, results in each of the sensors on the implant collecting data during this time period and then, at the end of the period, reporting the data out on respective signals 130 at different times over the next 0.5 to 2 seconds so that with one interrogation signal 128, the data from all sensors 22 is collected.

The interrogation module 124 is operating under control of the control unit 126 which has a microprocessor for the controller, a memory, an I/O circuit to interface with the interrogation module and a power supply. The control unit may output data to a computer or other device for display and use by the physician to treat the subject.

FIG. 6 illustrates the operation according to a one embodiment within a subject. The subject has an outer skin 132. As illustrated in FIG. 6, the interrogation module 124 and control unit 126 are positioned outside the skin 132 of the subject. The interrogation signal 128 passes through the skin of the subject with a wireless RF signal, and the data is received on a wireless RF signal 130 from the sensors within the implant 10 back to the interrogation module 124. While the wireless signal can be in any frequency range, an RF range is preferred. A frequency in the VLF to LF ranges of between 3-1300 kHz is preferred to permit the signal to be carried to sufficient depth inside the body with low power, but frequencies below 3 kHz and above 1300 kHz can also be used. The sensing does not require a transfer of large amounts of data and low power is preferred; therefore, a low frequency RF signal is acceptable. This also avoids competition from and inadvertent activation by other wireless signal generators, such as blue tooth, cell phones and the like.

Figure 7:
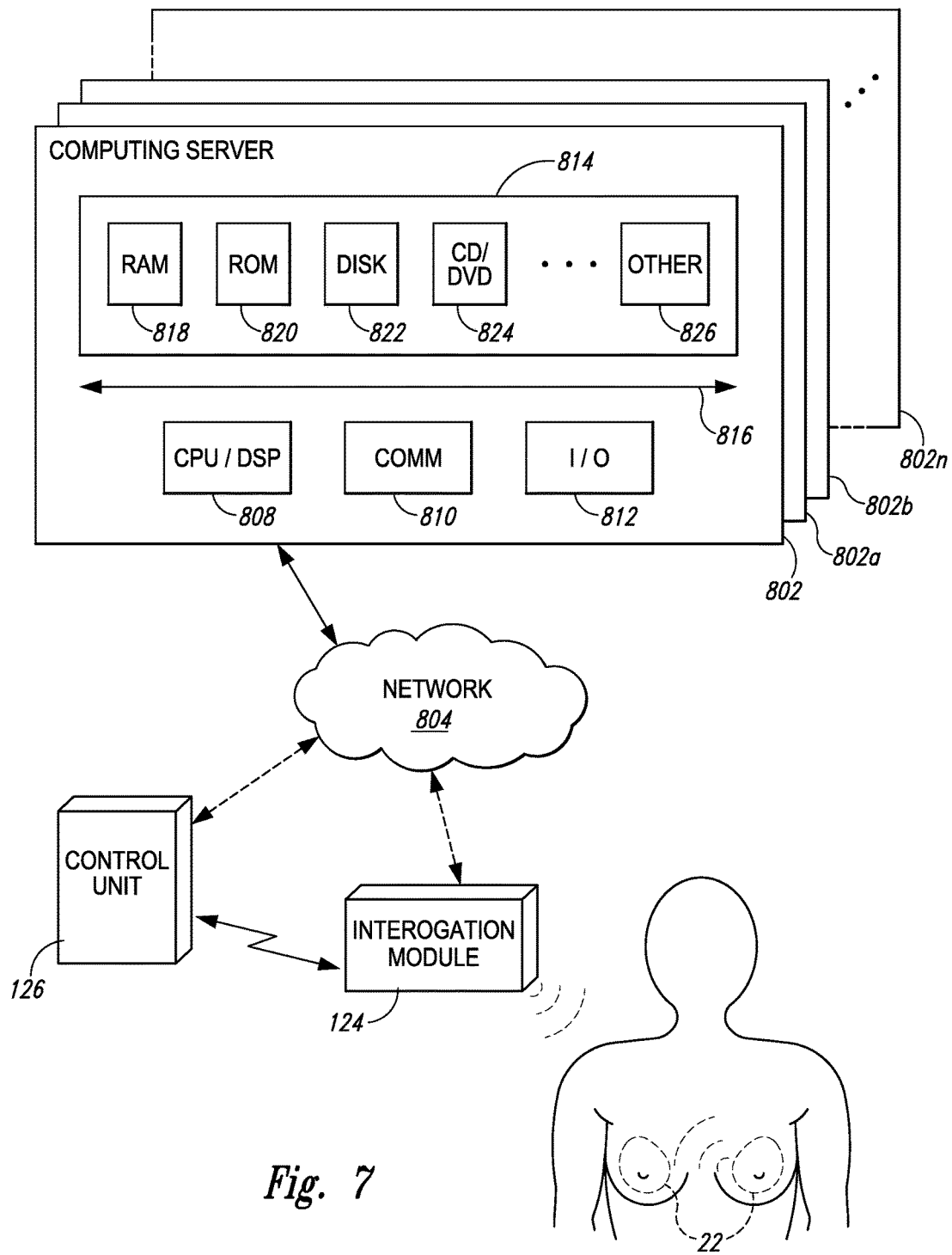
FIG. 7 is a schematic illustration of one or more sensors positioned on the implant within a subject which is being probed for data and outputting data, according to one embodiment of the invention.

H. Collection, Transmission, Analysis, and Distribution of Data from Assemblies Comprising Implants FIG. 7 illustrates one embodiment of an information and communication technology (ICT) system 800 arranged to process sensor data (e.g., data from the sensors 22). In FIG. 7, the ICT system 800 is illustrated to include computing devices that communicate via a network 804, however in other embodiments, the computing devices can communicate directly with each other or through other intervening devices, and in some cases, the computing devices do not communicate at all. The computing devices of FIG. 7 include computing servers 802, control units 126, interrogation units 124, and other devices that are not shown for simplicity.

In FIG. 7 one or more sensors 22 communicate with an interrogation module 124. The interrogation module 124 of FIG. 7 is directed by a control unit 126, but in other cases, interrogation modules 124 operates autonomously and passes information to and from sensors 22. One or both of the interrogation module 124 and control unit 126 can communicate with the computing server 802.

Within certain embodiments, the interrogation module and/or the control unit may be a wearable device on the subject. The wearable device (e.g., a watch-like device, a wrist-band, a bra, or other device that may be carried or worn by the subject) can interrogate the sensors over a set (or random) period of time, collect the data, and forward the data on to one or more networks (804). Furthermore, the wearable device may collect data of its own accord which can also be transmitted to the network. Representative examples of data that may be collected include location (e.g., a GPS), body or skin temperature, and other physiologic data (e.g., pulse, glucose, etc.). Within yet other embodiments, the wearable device may notify the subject directly of any of a number of prescribed conditions, including but not limited to possible or actual failure of the implant.

The information that is communicated between an interrogation module 124 and the sensors 22, may be useful for many purposes as described herein. In some cases, for example, sensor data information is collected and analyzed expressly for the health of an individual subject. In other cases, sensor data is collected and transmitted to another computing device to be aggregated with other data (for example, the sensor data from 22 may be collected and aggregated with other data collected from a wearable device (e.g., a device that may, in certain embodiments, include GPS data and the like).

FIG. 7 illustrates aspects of a computing server 802 as a cooperative bank of servers further including computing servers 802a, 802b, and one or more other servers 802n. It is understood that computing server 802 may include any number of computing servers that operate individually or collectively to the benefit of users of the computing servers.

In some embodiments, the computing servers 802 are arranged as cloud computing devices created in one or more geographic locations, such as the United States and Canada. The cloud computing devices may be created as MICROSOFT AZURE cloud computing devices or as some other virtually accessible remote computing service.

An interrogation module 124 and a control unit 126 are optionally illustrated as communicating with a computing server 802. Via the interrogation module 124 or control unit 126, sensor data is transferred to (and in addition or alternatively from) a computing server 802 through network 804.

The network 804 includes some or all of cellular communication networks, conventional cable networks, satellite networks, fiber-optic networks, and the like configured as one or more local area networks, wide area networks, personal area networks, and any other type of computing network. In a preferred embodiment, the network 804 includes any communication hardware and software that cooperatively works to permit users of computing devices to view and interact with other computing devices.

Computing server 802 includes a central processing unit (CPU) digital signal processing unit (DSP) 808, communication modules 810, Input/Output (I/O) modules 812, and storage module 814. The components of computing server 802 are cooperatively coupled by one or more buses 816 that facilitate transmission and control of information in and through computing server 802. Communication modules 810 are configurable to pass information between the computer server 802 and other computing devices (e.g., computing servers 802a, 802b, 802n, control unit 126, interrogation unit 124, and the like). I/O modules 812 are configurable to accept input from devices such as keyboards, computer mice, trackballs, and the like. I/O modules 812 are configurable to provide output to devices such as displays, recorders, LEDs, audio devices, and the like.

Storage module 814 may include one or more types of storage media. For example, storage module 814 of FIG. 7 includes random access memory (RAM) 818, read only memory (ROM) 810, disk based memory 822, optical based memory 8124, and other types of memory storage media 8126. In some embodiments one or more memory devices of the storage module 814 has configured thereon one or more database structures. The database structures may be used to store data collected from sensors 22.

In some embodiments, the storage module 814 may further include one or more portions of memory organized a non-transitory computer-readable media (CRM). The CRM is configured to store computing instructions executable by a CPU 808. The computing instructions may be stored as one or more files, and each file may include one or more computer programs. A computer program can be standalone program or part of a larger computer program. Alternatively or in addition, each file may include data or other computational support material for an application that directs the collection, analysis, processing, and/or distribution of data from sensors (e.g., implant sensors). The sensor data application typically executes a set of instructions stored on computer-readable media.

It will be appreciated that the computing servers shown in the figures and described herein are merely illustrative and are not intended to limit the scope of the present invention. Computing server 802 may be connected to other devices that are not illustrated, including through one or more networks such as the Internet or via the Web that are incorporated into network 804. More generally, a computing system or device (e.g., a "client" or "server") or any part thereof may comprise any combination of hardware that can interact and perform the described types of functionality, optionally when programmed or otherwise configured with software, including without limitation desktop or other computers, database servers, network storage devices and other network devices, PDAs, cell phones, glasses, wrist bands, wireless phones, pagers, electronic organizers, Internet appliances, television-based systems (e.g., using set-top boxes and/or personal/digital video recorders), and various other products that include appropriate inter-communication capabilities. In addition, the functionality provided by the illustrated system modules may in some embodiments be combined in fewer modules or distributed in additional modules. Similarly, in some embodiments the functionality of some of the illustrated modules may not be provided and/or other additional functionality may be available.

In addition, while various items are illustrated as being stored in memory or on storage while being used, these items or portions of them can be transferred between memory and other storage devices for purposes of memory management and/or data integrity. In at least some embodiments, the illustrated modules and/or systems are software modules/systems that include software instructions which, when executed by the CPU/DSP 808 or other processor, will program the processor to automatically perform the described operations for a module/system. Alternatively, in other embodiments, some or all of the software modules and/or systems may execute in memory on another device and communicate with the illustrated computing system/device via inter-computer communication.

Furthermore, in some embodiments, some or all of the modules and/or systems may be implemented or provided in other manners, such as at least partially in firmware and/or hardware means, including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), and the like. Some or all of the systems, modules, or data structures may also be stored (e.g., as software instructions or structured data) on a transitory or non-transitory computer-readable storage medium 814, such as a hard disk 822 or flash drive or other non-volatile storage device 8126, volatile 818 or non-volatile memory 810, a network storage device, or a portable media article (e.g., a DVD disk, a CD disk, an optical disk, a flash memory device, etc.) to be read by an appropriate input or output system or via an appropriate connection. The systems, modules, and data structures may also in some embodiments be transmitted as generated data signals (e.g., as part of a carrier wave or other analog or digital propagated signal) on a variety of computer readable transmission mediums, including wireless-based and wired/cable-based mediums. The data signals can take a variety of forms such as part of a single or multiplexed analog signal, as multiple discrete digital packets or frames, as a discrete or streaming set of digital bits, or in some other form. Such computer program products may also take other forms in other embodiments. Accordingly, the present invention may be practiced with other computer system configurations.

In FIG. 7, sensor data from, e.g., sensors 22 is provided to computing server 802. Generally speaking, the sensor data, represents data retrieved from a known subject and from a known sensor. The sensor data may possess include or be further associated with additional information such as the USI, UDI, a time stamp, a location (e.g., GPS) stamp, a date stamp, and other information. The differences between various sensors is that some may include more or fewer data bits that associate the data with a particular source, collection device, transmission characteristic, or the like.

In some embodiments, the sensor data may comprise sensitive information such as private health information associated with a specific subject. Sensitive information, for example sensor data from sensors e.g., 22, may include any information that an associated party desires to keep from wide or easy dissemination. Sensitive information can stand alone or be combined with other non-sensitive information. For example, a subject's medical information is typically sensitive information. In some cases, the storage and transmission of a subject's medical information is protected by a government directive (e.g., law, regulation, etc.) such as the U.S. Health Insurance Portability and Accountability Act (HIPPA).

As discussed herein, a reference to "sensitive" information includes information that is entirely sensitive and information that is some combination of sensitive and non-sensitive information. The sensitive information may be represented in a data file or in some other format. As used herein, a data file that includes a subject's medical information may be referred to as "sensitive information." Other information, such as employment information, financial information, identity information, and many other types of information may also be considered sensitive information.

A computing system can represent sensitive information with an encoding algorithm (e.g., ASCII), a well-recognized file format (e.g., PDF), or by some other format. In a computing system, sensitive information can be protected from wide or easy dissemination with an encryption algorithm.

Generally speaking, sensitive information can be stored by a computing system as a discrete set of data bits. The set of data bits may be called "plaintext." Furthermore, a computing system can use an encryption process to transform plaintext using an encryption algorithm (i.e., a cipher) into a set of data bits having a highly unreadable state (i.e., cipher text). A computing system having knowledge of the encryption key used to create the cipher text can restore the information to a plaintext readable state. Accordingly, in some cases, sensitive data (e.g., sensor data 806a, 806b) is optionally encrypted before being communicated to a computing device.

In one embodiment, the operation of the information and communication technology (ICT) system 800 of FIG. 7 includes one or more sensor data computer programs stored on a computer-readable medium. The computer program may optionally direct and/or receive data from one or more implant sensors implanted in one or more subjects. A sensor data computer program may be executed in a computing server 802. Alternatively, or in addition, a sensor data computer program may be executed in a control unit 126, an interrogation unit 124.

In one embodiment, a computer program to direct the collection and use of implant sensor data is stored on a non-transitory computer-readable medium in storage module 814. The computer program is configured to identify a subject who has a wireless implant inserted in his or her body. The wireless implant may include one or more wireless sensors.

In some cases, the computer program identifies one subject, and in other cases, two or more subjects are identified. The subjects may each have one or more wireless implants, and each wireless implant may have one or more wireless sensors of the type described herein.

The computer program is arranged to direct the collection of sensor data from the wireless implant devices. The sensor data is generally collected with a wireless interrogation unit 124. In some cases, the program communicates with the wireless interrogation unit 124. In other cases, the program communicates with a control unit 126, which in turn directs a wireless interrogation unit 124. In still other cases, some other mechanism is used direct the collection of the sensor data.

Once the sensor data is collected, the data may be further processed. For example, in some cases, the sensor data includes sensitive subject data, which can be removed or disassociated with the data. The sensor data can be individually stored (e.g., by unique sensor identification number, device number, etc.) or aggregated together with other sensor data by sensor type, time stamp, location stamp, date stamp, subject type, other subject characteristics, or by some other means.

The following pseudo-code description is used to generally illustrate one exemplary algorithm executed by a computing server 802 and generally described herein with respect to FIG. 7:

```
Start
Open a secure socket layer (SSL)
Identify a subject
Communicate with a predetermined control unit
Request sensor data from the subject via the control unit
Receive sensor data
If the sensor data is encrypted
    THEN decrypt the sensor data
Store encrypted data in the selected storage locations
Aggregate the sensor data with other sensor data
Store encrypted data in the selected storage locations
Maintain a record of the storage transaction
Perform post storage actions
End
```

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, ambulance, truck, locomotive, tank, armored personnel carrier, etc.), (c) a building (e.g., a home, hospital, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., AT&T, T-Mobile, Verizon.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

In conclusion, implants utilizing a variety of sensors can be utilized to serve a variety of critical clinical functions, such as safe, accurate and less traumatic placement and deployment of the implant, procedural and post-operative "real time" imaging of the implant and the surrounding anatomy, the early identification of the development of implant complications (often prior to becoming evident by other medical diagnostic procedures), and the patient's overall health status and response to treatment. Currently, post-operative (both in hospital and out-patient) evaluation of implant patients is through patient history, physical examination and medical monitoring that is supplemented with diagnostic imaging studies as required. However, most of the patient's recuperative period occurs between hospital and office visits and the majority of data on daily function goes uncaptured; furthermore, monitoring patient progress through the use of some diagnostic imaging technology can be expensive, invasive and carry its own health risks (the use of nuclear isotopes or certain dyes, radiation exposure). It can, therefore, be very difficult to accurately measure and follow the development or worsening of symptoms and evaluate "real life" implant performance, particularly as they relate to patient activity levels, exercise tolerance, and the effectiveness of rehabilitation efforts and medications.

At present, neither the physician nor the patient has access to the type of "real time," continuous, objective, implant performance measurements that they might otherwise like to have. Being able to monitor in situ implant function, integrity, anatomy and physiology can provide the physician with valuable objective information during office visits; furthermore, the patient can take additional readings at home at various times (e.g. when experiencing pain, during exercise, after taking medications, etc.) to provide important complementary clinical information to the doctor (which can be sent to the healthcare provider electronically even from remote locations). From the perspective of the patient, being able to monitor many of these same parameters at home allows them to take a more proactive role in their care and recovery and provide him or her with either an early warning indicator to seek medical assistance or with reassurance.

In one alternative, the patient may have a reading device in their home which collates the data from the implant on a periodic basis, such as once per day or once per week. In addition to empowering the patient to follow their own rehabilitation—and enabling them to see the positive (and negative) effects of various lifestyle choices on their health and rehabilitation—such information access can be expected to improve compliance and improve patient outcomes. Furthermore, their recovery experience can be shared via the web with other patients to compare their progress versus expected "norms" for function and rehabilitation and alert them to signs and symptoms that should be brought to their doctor's attention. From a public health perspective, the performance of different implants can be compared in different patients (different sexes, disease severity, activity levels, concurrent diseases such as hypertension and diabetes, smoking status, obesity, etc.) to help manufacturers design better implants and assist physicians in the selection of the right implant for a specific patient types. Payers, patients, manufacturers and physicians could all benefit from the collection of this comparative information. Poor and dangerous products could be identified and removed from the market and objective long-term effectiveness data collected and analyzed. Lastly, data accumulated at home can be collected and transmitted via the Internet to the physician's office for analysis—potentially eliminating unnecessary visits in some cases and encouraging immediate medical follow-up in others.

Conventions

In general, and unless otherwise specified, all technical and scientific terms used herein shall have the same meaning as those commonly understood by one of ordinary skill in the art to which the embodiment pertains. For convenience, the meanings of selected terms are provided below, where these meanings are provided in order to aid in describing embodiments identified herein. Unless stated otherwise, or unless implicit from the context in which the term is used, the meanings provided below are the meanings intended for the referenced term.

Embodiment examples or feature examples specifically provided are intended to be exemplary only, that is, those examples are non-limiting on an embodiment. The term "e.g." (latin, exempli gratia) is used herein to refer to a non-limiting example, and effectively means "for example".

Singular terms shall include pluralities and plural terms shall include the singular, unless otherwise specified or required by context. For example, the singular terms "a", "an" and "the" include plural referents unless the context clearly indicates otherwise. Similarly, the term "or" is intended to include "and" unless the context clearly indicates otherwise.

Except in specific examples provided herein, or where otherwise indicated, all numbers expressing quantities of a component should be understood as modified in all instances by the term "about", where "about" means±5% of the stated value, e.g., 100 refers to any value within the range of 95-105.

The terms comprise, comprising and comprises are used to identify essential features of an embodiment, where the embodiment may be, for example, a composition, device, method or kit. The embodiment may optionally contain one or more additional unspecified features, and so the term comprises may be understood to mean includes.

The following are some specific numbered embodiments of the systems and processes disclosed herein. These embodiments are exemplary only. It will be understood that the invention is not limited to the embodiments set forth herein for illustration, but embraces all such forms thereof as come within the scope of the above disclosure.

1) An implantable medical device, comprising an aesthetic implant, and a sensor.

2) The implantable medical device according to embodiment 1 wherein said aesthetic implant is a breast implant.

3) The implantable medical device according to embodiment 1 wherein said aesthetic implant is a nose implant.

4) The implantable medical device according to embodiment 1 wherein said aesthetic implant is a chin implant.

5) The implantable medical device according to embodiment 1 wherein said aesthetic implant is a bicep or tricep implant.

6) The implantable medical device according to embodiment 1 wherein said aesthetic implant is a buttock implant.

7) The implantable medical device according to embodiment 1 wherein said aesthetic implant is a calf implant.

8) The medical device according to any one of embodiments 1 to 7 wherein said sensor is located within said implant.

9) The medical device according to any one of embodiments 1 to 7 wherein said sensor is located on said implant.

10) The medical device according to any one of embodiments 1 to 9 wherein said device is sterile.

11) The medical device according to any one of embodiments 1 to 10 wherein said sensor is a contact sensor.

12) The medical device according to any one of embodiments 1 to 11 wherein said sensor is a pressure sensor.

13) The medical device according to any one of embodiments 1 to 12 wherein said sensor is an accelerometer sensor.

14) The medical device according to embodiment 13 wherein said accelerometer detects acceleration, tilt, vibration, shock and or rotation.

15) The medical device according to any one of embodiments 1 to 14 wherein said sensor is a temperature sensor.

16) The medical device according to any one of embodiments 1 to 15 wherein said sensor is a mechanical stress sensor.

17) The medical device according to any one of embodiments 1 to 16 wherein said sensor is selected from the group consisting of position sensors, chemical microsensors, and tissue metabolic sensors.

18) The medical device according to any one of embodiments 1 to 17 further comprising:
an electronic processor positioned upon and/or inside the implant or medical device that is electrically coupled to sensors.

19) The medical device according to embodiment 18 wherein the electric coupling is a wireless coupling.

20) The medical device according to embodiment 18 further including:
a memory coupled to the electronic processor and positioned upon and/or inside the implant or medical device.

21) The medical device according to any one of embodiments 1 to 20 wherein said sensor is a plurality of sensors which are positioned on or within said medical device at a density of greater than 1, 2, 3, 4, 5, 6, 7, 8, 9, 10 or 20 sensors per square centimeter.

22) The medical device according to any one of embodiments 1 to 20 wherein said sensor is a plurality of sensors which are positioned on or within said medical device at a density of greater than 1, 2, 3, 4, 5, 6, 7, 8, 9, 10 or 20 sensors per cubic centimeter.

23) A method comprising:
obtaining data from sensors positioned at a plurality of locations between on and/or within the medical device according to any one of embodiments 1 to 23 of a patient;
storing the data in a memory device located on or within the medical device; and
transferring the data from the memory to a location outside the medical device.

24) The method according to embodiment 27 further comprising the step of analyzing said data.

25) A method for detecting and/or recording an event in a subject with the medical device according to any one of embodiments 1 to 23, comprising the step of interrogating at a desired point in time the activity of one or more sensors within the medical device, and recording said activity.

26) The method according to embodiment 25 wherein the step of interrogating is performed by a subject which has said medical device.

27) The method according to embodiment 25 or 26 wherein said recording is performed on a wearable device.

28) The method according to any one of embodiments 25 to 27, wherein said recording, or a portion thereof, is provided to a health care provider.

29) A method for imaging the medical device in an implant, comprising the steps of
 (a) detecting the location of one or more sensors in the medical device according to any one of embodiments 1 to 23; and
 (b) visually displaying the location of said one or more sensors, such that an image of the medical device is created.

30) The method according to embodiment 29 wherein the step of detecting occurs over time.

31) The method according to embodiment 29 or 30, wherein said visual display shows changes in the positions of said sensors over time, and/or changes in temperature of the sensors or surrounding tissue over time.

32) The method according to any one of embodiments 29 to 31 wherein said visual display is a three-dimensional image of said medical device.

33) A method for inserting the implant according to any one of embodiments 1 to 23, comprising the steps of
 (a) inserting an implantable medical device according to any one of embodiments 1 to 23 into a subject; and
 (b) imaging the placement of said medical device according to the method of an one of embodiments 29 to 32.

34) A method for examining the implant according to any one of embodiments 1 to 23 which has been previously inserted into a patient, comprising the step of imaging the implant according to the method of any one of embodiments 29 to 32.

35) A method of monitoring an implant within a subject, comprising:
 transmitting a wireless electrical signal from a location outside the body to a location inside the subject's body;
 receiving the signal at a sensor positioned on an implant according to any one of embodiments 1 to 23 located inside the body;
 powering the sensor using the received signal;
 sensing data at the sensor; and
 outputting the sensed data from the sensor to a receiving unit located outside of the body.

36) The method according to embodiment 35 wherein said receiving unit is a watch, wrist band, cell phone or glasses.

37) The method according to embodiments 35 or 36 wherein said receiving unit is located within a subject's residence or office.

38) The method according to embodiments any one of embodiments 35 to 37 wherein said sensed data is provided to a health care provider.

39) The method according to any one of embodiments 35 to 38 wherein said sensed data is posted to one or more websites.

40) A non-transitory computer-readable storage medium whose stored contents configure a computing system to perform a method, the method comprising:
 identifying a subject, the identified subject having at least one wireless implant according to any one of embodiments 1 to 23, each wireless implant having one or more wireless sensors;
 directing a wireless interrogation unit to collect sensor data from at least one of the respective one or more wireless sensors; and
 receiving the collected sensor data.

41) The non-transitory computer-readable storage medium of embodiment 40 whose stored contents configure a computing system to perform a method, the method further comprising:
 identifying a plurality of subjects, each identified subject having at least one wireless implant, each wireless implant having one or more wireless sensors;
 directing a wireless interrogation unit associated with each identified subject to collect sensor data from at least one of the respective one or more wireless sensors;
 receiving the collected sensor data; and
 aggregating the collected sensor data.

42) The non-transitory computer-readable storage medium of embodiment 41 whose stored contents configure a computing system to perform a method, the method further comprising:
 removing sensitive subject data from the collected sensor data; and
 parsing the aggregated data according to a type of sensor.

43) The non-transitory computer-readable storage medium of embodiment 42 whose stored contents configure a computing system to perform a method, wherein directing the wireless interrogation unit includes directing a control unit associated with the wireless interrogation unit.

44) The non-transitory computer readable storage medium according to any one of embodiments 40 to 43, wherein said implant is according to any one of embodiments 1 to 23.

45) The storage medium according to any one of embodiments 40 to 44 wherein said collected sensor data is received on a watch, wrist band, cell phone or glasses.

46) The storage medium according to any one of embodiments 40 to 45 wherein said collected sensor data is received within a subject's residence or office.

47) The storage medium according to any one of embodiments 40 to 46 wherein said collected sensed data is provided to a health care provider.

48) The storage medium according to any one of embodiments 40 to 47 wherein said sensed data is posted to one or more websites.

49) The method according to any one of embodiments 35 to 39, or storage medium according to any one of embodiments 40 to 47, wherein said data is analyzed.

50) The method or storage medium according to embodiment 49 wherein said data is plotted to enable visualization of change over time.

51) The method or storage medium according to embodiments 49 or 50 wherein said data is plotted to provide a three-dimensional image.

52) A method for determining degradation of an implant, comprising the steps of a) providing to a subject an implant according to any one of embodiments 1 to 23, and b) detecting a change in a sensor, and thus determining degradation of the implant.

53) The method according to embodiment 52 wherein said sensor is capable of detecting one or more physiological and/or locational parameters.

54) The method according to embodiments 52 or 53 wherein said sensor detects a location within the subject.

55) The method according to any one of embodiments 52 to 54 wherein said sensor moves from its original location, thereby indicating degradation of the implant.

56) The method according to any one of embodiments 52 to 55 wherein the step of detecting is a series of detections over time.

57) A method for determining an infection associated with an implant, comprising the steps of a) providing to a subject an implant according to any one of embodiments 1 to 23, wherein said implant comprises at least one temperature sensor and/or metabolic sensor, and b) detecting a change in said temperature sensor and/or metabolic sensor, and thus determining the presence of an infection.

58) The method according to embodiment 57 wherein the step of detecting is a series of detections over time.

59) The method according to embodiments 57 or 58 wherein said change is greater than a 1% change over the period of one hour.

60) The method according to any one of embodiments 57 to 59 wherein said change is a continually increasing temperature and/or metabolic activity over the course of 4 hours.

The various embodiments described above can be combined to provide further embodiments. All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method comprising:
(a) providing a first implantable medical device comprising a first breast implant and a plurality of first sensors selected from a position sensor that measures position and can output data and an accelerometer sensor that measures acceleration and can output data, where the plurality of first sensors are located on or within the first breast implant;
(b) inserting the first implantable medical device into a surrounding implant located within an implant pocket of a patient to provide a first implanted medical implant located within the patient, where the surrounding implant is selected from the group consisting of a gel, an adhesion barrier, a hemostat, a glue, and an adhesive, where the surrounding implant is located in the implant pocket such that it lies between the first implanted medical device and a patient tissue;
(c) imaging the first implantable medical device during surgical placement of the first implantable medical device but prior to finally implanting the first implantable medical device in the patient to provide an image thereof, the imaging comprising detecting locations of the plurality of first sensors; where the detecting comprises the step of interrogating at a desired point in time an activity of the plurality of first sensors, and recording said activity in a memory; and
(d) visually displaying the location of the plurality of first sensors such that an image of the first implantable medical device is created while inserting the first implantable medical device into the patient.

2. The method of claim 1 wherein the image provides information about an anatomical placement of the first implantable medical device in the patient.

3. The method of claim 1 further comprising:
(e) providing a second implantable medical device comprising a second breast implant and a second sensor, where the second sensor is located on or within the second breast implant;
(f) inserting the second implantable medical device into the patient to provide a second implanted medical implant located within the patient;
(g) imaging the second implantable medical device while inserting the second implantable medical device into the patient to provide an image thereof, the imaging comprising detecting the second sensor and identifying a location of the second sensor; and
(h) visually displaying the location of the second sensor such that an image of the second implantable medical device is created during inserting the second implantable medical device into the patient.

4. The method of claim 3 wherein the images of the first and second implantable medical devices provide information about a bilateral symmetry of the first and second implantable medical devices located within the patient.

5. The method of claim 1 wherein the plurality of first sensors are located within a filing of the first breast implant.

6. The method of claim 1 wherein the plurality of first sensors are located on or within a shell of the first breast implant.

7. The method of claim 1 wherein the plurality of first sensors comprise a plurality of position sensors.

8. The method of claim 1 wherein the plurality of first sensors comprise a plurality of accelerometers.

9. The method of claim 1 wherein the plurality of first sensors comprise a plurality of passive wireless sensors.

10. The method of claim 1 wherein the first implantable medical device further comprises one or more processor circuits, CPUs, memory chips, and antennas for sending and receiving data from the plurality of first sensors.

11. The method of claim 10 wherein an interrogation module outputs a wireless signal comprising an interrogation request to the plurality of first sensors; the plurality of first sensors receive the interrogation request and perform a sensing to obtain data; and the data is output wirelessly to the interrogation module.

12. The method of claim 11 wherein the interrogation module operates under control of a control unit comprising a microprocessor, a memory, an input/output circuit and a power supply, where the data is transmitted from the interrogation module to the control unit, and the data is transmitted from the control unit to a computer or other device for display.

13. The method of claim 1 wherein the first implanted medical device further comprises one or more processor circuits, CPUs, memory chips, and antennas for sending and receiving data from the plurality of first sensors.

14. The method of claim 13 wherein an interrogation module outputs a wireless signal comprising an interrogation request to the plurality of first sensors; the plurality of first sensors receive the interrogation request and perform a sensing to obtain data; and the data is output wirelessly to the interrogation module.

15. The method of claim 14 wherein the interrogation module operates under control of a control unit comprising a microprocessor, a memory, an input/output circuit and a power supply, where the data is transmitted from the interrogation module to the control unit, and the data is transmitted from the control unit to a computer or other device for display.

16. The method of claim 15 wherein the interrogation request is output to the plurality of first sensors during insertion of the first implantable medical device into the patient.

\* \* \* \* \*